United States Patent
Raslambekov

(10) Patent No.: US 11,730,568 B2
(45) Date of Patent: *Aug. 22, 2023

(54) SYSTEMS AND METHODS FOR DETERMINING AN ORTHODONTIC TREATMENT

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

This patent is subject to a terminal disclaimer.

(21) Appl. No.: 17/667,715

(22) Filed: Feb. 9, 2022

(65) Prior Publication Data

US 2022/0387138 A1    Dec. 8, 2022

Related U.S. Application Data

(63) Continuation of application No. 17/338,143, filed on Jun. 3, 2021, now Pat. No. 11,259,897.

(51) Int. Cl.
*G06T 15/00* (2011.01)
*A61C 7/00* (2006.01)
*G06T 17/20* (2006.01)

(52) U.S. Cl.
CPC ............ *A61C 7/002* (2013.01); *G06T 17/20* (2013.01); *G06T 2210/41* (2013.01)

(58) Field of Classification Search
CPC .......... G06F 19/30; G06F 19/32; G06F 19/34; A61C 7/002; A61C 9/0046; A61C 2007/004; G06Q 50/22; G06Q 50/24
(Continued)

(56) References Cited

U.S. PATENT DOCUMENTS 6,471,511 B1    10/2002    Chishti et al.
6,736,638 B1    5/2004    Sachdeva et al.
(Continued)

FOREIGN PATENT DOCUMENTS

CN    110916820 A    3/2020

OTHER PUBLICATIONS

Pratiwi et al.,"Simulation of Stress Distribution on the Upper First Molar and Alveolar Bone with the Transpalatal Arch and Upper Second Molar Using Finite Element Analysis", Published on Jul. 1, 2019, Pesquisa Brasileira em Odontopediatria e Clínica Integrada.
(Continued)

*Primary Examiner* — Phu K Nguyen
(74) *Attorney, Agent, or Firm* — BCF LLP

(57) ABSTRACT

Methods and systems for determining orthodontic treatment based on 3D digital model of subject's teeth. The method includes determining, for a given trajectory segment of the orthodontic treatment of a given tooth in which the given tooth is moved from a start position to an end position, whether the force required to move the given tooth from the start position to the end position causes an induced stress associated with at least one other of the plurality of subject's teeth. In response to the induced stress being outside of a predetermined threshold level, determining a counter force to be applied to the at least one other of the plurality of subject's teeth. The orthodontic treatment can be thus determined as including the force to be applied to the given tooth and the determined counter force to be applied to the at least one other of the plurality if subject's teeth.

17 Claims, 12 Drawing Sheets

(58) Field of Classification Search
USPC .......................................................... 345/418
See application file for complete search history.

(56) References Cited

U.S. PATENT DOCUMENTS

| | | | |
|---|---|---|---|
| 6,739,870 B2 | 5/2004 | Lai et al. | |
| 7,320,592 B2 | 1/2008 | Chishti et al. | |
| 7,930,189 B2 | 4/2011 | Kuo | |
| 7,972,134 B2 | 7/2011 | Lai et al. | |
| 8,874,452 B2 | 10/2014 | Kuo | |
| 8,899,977 B2 | 12/2014 | Cao et al. | |
| 9,161,823 B2 | 10/2015 | Morton et al. | |
| 9,220,580 B2 | 12/2015 | Borovinskih et al. | |
| 9,492,245 B2 | 11/2016 | Sherwood et al. | |
| 10,426,575 B1 | 10/2019 | Raslambekov | |
| 10,463,452 B2 | 11/2019 | Matov et al. | |
| 10,603,137 B2 | 3/2020 | Allauddin et al. | |
| 10,650,517 B2 | 5/2020 | Parpara et al. | |
| 10,695,146 B1 | 6/2020 | Raslambekov | |
| 10,695,147 B1 | 6/2020 | Raslambekov | |
| 10,717,208 B1 | 7/2020 | Raslambekov | |
| 10,792,127 B2 | 10/2020 | Kopelman et al. | |
| 10,888,397 B1 | 1/2021 | Raslambekov | |
| 10,993,782 B1 | 5/2021 | Raslambekov | |
| 11,026,767 B1 | 6/2021 | Raslambekov | |
| 11,065,085 B2 | 7/2021 | Martz et al. | |
| 11,259,897 B1 * | 3/2022 | Raslambekov | G16H 30/20 |
| 11,571,279 B2 * | 2/2023 | Wang | G06F 17/18 |
| 2019/0102880 A1 * | 4/2019 | Parpara | G06T 17/10 |
| 2019/0159871 A1 | 5/2019 | Chan et al. | |
| 2019/0231480 A1 * | 8/2019 | Moore, III | B33Y 70/00 |
| 2019/0321136 A1 | 10/2019 | Martz et al. | |
| 2020/0100871 A1 * | 4/2020 | Wang | G01N 33/442 |
| 2020/0214598 A1 | 7/2020 | Li et al. | |
| 2020/0214801 A1 | 7/2020 | Wang et al. | |

OTHER PUBLICATIONS

Penedo et al.,"3D simulation of orthodontic tooth movement", Published on Oct. 2008, Dental Press Journal of Orthodontics, pp. 98-108.

Fercec et al.,"Determination of stresses and forces on the orthodontic system by using numerical simulation of the finite elements method", Published in Oct. 2012, vol. 122, Issue 4.

* cited by examiner

SYSTEMS AND METHODS FOR DETERMINING AN ORTHODONTIC TREATMENT

CROSS-REFERENCE

The present application is a Continuation of U.S. patent application Ser. No. 17/338,143 filed on Jun. 3, 2021, the content of which is incorporated herein by reference in its entirety.

FIELD

The present technology relates to systems and methods for determining an orthodontic treatment for a patient.

BACKGROUND

Planning an orthodontic treatment for a patient may include determining a desired position of one or more teeth of a subject to obtain a desired configuration of the teeth in an arch form of the subject. The planned orthodontic treatment may include determining a trajectory of movement of one or more given teeth of the arch form of the subject to a target position in one or more treatment steps. The so determined orthodontic treatment may then be implemented by applying one or more orthodontic devices to the patient's teeth to exert an external force, over the one or more treatments, to the one or more given teeth to cause each respective tooth to move along a given determined tooth trajectory towards the target position.

However, it is important that the determined orthodontic treatment takes into account safety of the orthodontic treatment in terms of avoiding or minimizing pain and/or damage to the teeth or other tissues of the patient. A contrasting requirement is that the orthodontic treatment is efficient and minimizes an overall duration of the orthodontic treatment.

Certain prior art approaches have been proposed regarding the generation of teeth trajectories for the given tooth.

U.S. Pat. No. 9,161,823-B2 issued on Oct. 20, 2015, assigned to Align Technology Inc., and entitled "Orthodontic systems and methods including parametric attachments" discloses orthodontic systems and related methods for designing and providing improved or more effective tooth moving systems for eliciting a desired tooth movement and/or repositioning teeth into a desired arrangement. The methods and orthodontic systems include tooth attachments having improved or optimized parameters selected or modified for more optimal and/or effective application of forces for a desired/selected orthodontic movement. Attachments can be customized to a particular patient, a particular movement, and/or a sub-group or sub-set of patients, and configured to engage an orthodontic tooth positioning appliance worn by a patient, where engagement between the attachment and orthodontic appliance results in application of a repositioning force or series/system of forces to the tooth having the attachment and will generally elicit a tooth movement.

U.S. Pat. No. 6,739,870-B2 issued on May 25, 2004, assigned to 3M Innovative Properties Co., and entitled "Use of finite element analysis for orthodontic mechanics and appliance selection" discloses determining an effective orthodontic treatment by storing an original position model of a patient's teeth. The patient's teeth are then displayed according to the original position model, and appliances are selected according to a proposed orthodontic treatment. A final position model of the patient's teeth is also stored, and the selected appliances are displayed based upon the final position model. A finite element analysis is performed based on the proposed orthodontic treatment and on a movement of the patient's teeth from the final position to the original position in order to determine stresses, strains, forces, and/or moments on the appliances and on the patient's teeth and bone. If the stresses, strains, forces, and/or moments are not optimized, a new orthodontic treatment is proposed and the process is repeated.

SUMMARY

It is an object of the present technology to ameliorate at least some of the inconveniences present in the prior art.

The developers of the present technology have devised methods and systems for determining an orthodontic treatment which takes into account both efficiency requirements for minimizing the overall duration of the orthodontic treatment of the subject; and safety requirements aimed at preventing damage to the subject's teeth and other anatomical structures.

Furthermore, the methods and systems devised by the developers can reduce a required resource from a computer system implementing said methods and systems. This means that in certain embodiments even complex cases requiring many iterations can be performed.

More specifically, the developers have appreciated that the tooth trajectory may be represented by a plurality of treatment segments, wherein a given treatment segment corresponds to a treatment step having a predetermined treatment interval in which a predetermined force (referred to herein as "valid force") is applied to the given tooth to cause displacement of the given tooth.

In certain instances, the valid force applied to the given tooth may induce a movement in other teeth of the subject. Such movement may be undesired and/or unplanned for and may necessitate additional treatment segments to correct the movement of the other teeth, thus prolonging the overall treatment.

Thus, certain non-limiting embodiments of the present technology are directed to determining if there is any induced movement in other teeth of the subject based on the force applied to the given tooth. The orthodontic treatment may thus take into account a counter force to be applied to the other teeth to avoid or minimize their movement, or to direct a direction of their movement.

Thus, certain other non-limiting embodiments of the present technology are directed to determining the valid force based on an optimization of preliminary applied forces and preliminary trajectory segments which take into account induced stresses associated with other teeth of the patient (such as in periodontal ligaments (PDLs) thereof) and undesirable effects of these induced stresses. Undesirable effects of the induced stresses on the other teeth may include induced movement of the other teeth or damage to the PDLs of the other teeth, as well as damage to the given tooth or the other teeth. In this respect, developers have proposed utilizing stress thresholds associated with each teeth, such as a minimum stress threshold in the PDL below which a tooth will not move, and an maximum stress threshold above which there will be permanent or at least long lasting damage to the PDLs.

The so determined valid force can thus be used to determine a validated treatment segment as part of the orthodontic treatment, according to certain non-limiting embodiments of the present technology. In certain embodiments, the valid force is a modulated preliminary applied force to minimize or avoid the undesirable effects. In certain embodiments, the valid force is the same as the preliminary applied force but the preliminary treatment segment is modulated in that a counter force is applied to the other teeth while the valid force is being applied to the given tooth to minimize or avoid movement of the other teeth.

Accordingly, certain embodiments of the present technology are directed to manufacturing orthodontic appliances based on the validated treatment segment.

In certain embodiments, the validated treatment segment may ensure a maximum possible displacement of the given tooth whilst minimizing or preventing undesirable effects from induced stresses such as damage to the given tooth and other teeth, and undesired movement of the other teeth. By so doing, embodiments of the methods and systems described herein, may safely minimize a number of treatment segments, thereby reducing the overall duration of the orthodontic treatment. This may translate to a fewer number of associated orthodontic appliances to be applied to the subject's teeth in the course of the so planned orthodontic treatment. In certain embodiments, by avoiding or minimizing undesired movement of the other teeth during movement of the given tooth, a more effective and efficient orthodontic treatment may be attained.

More specifically, there is provided a method for determining an orthodontic treatment for a tooth of a subject, the method being executable by a processor of an electronic device, the method comprising: acquiring a 3D digital model of an arch form of the subject, the 3D digital model of the arch form including representations of a plurality of the subject's teeth including a 3D digital model of the given tooth; identifying an initial tooth position of the given tooth; acquiring an indication of a target tooth position for the given tooth; obtaining a trajectory of the given tooth from the initial tooth position to the target tooth position, the trajectory comprising a plurality of trajectory segments; for a given trajectory segment of the plurality of trajectory segments, applying a force to the 3D digital model of the given tooth to displace the given tooth from a start position to an end position of the trajectory segment within a predetermined time interval; determining whether the application of the force to the 3D digital model of the given tooth causes an induced stress associated with at least one other of the plurality of subject's teeth; in response to a determination that the induced stress is outside of a predetermined threshold level, determining a counter force to be applied to the at least one other of the plurality of subject's teeth; determining, for the given trajectory segment, the orthodontic treatment as including the force to be applied to the given tooth and the determined counter force to be applied to the at least one other of the plurality if subject's teeth; and storing data indicative of the orthodontic treatment in a memory communicatively coupled to the processor.

In certain embodiments, the predetermined threshold level comprises a minimum stress threshold above which the at least one other of the plurality of subject's teeth is caused to move.

In certain embodiments, the counter force is determined so as to reduce a movement of the at least one other of the plurality of subject's teeth.

In certain embodiments, the counter force is determined so as to direct a movement of the at least one other of the plurality of subject's teeth.

In certain embodiments, the method further comprises determining the force to be applied to the 3D digital model of the given tooth, the determining comprising: obtaining a minimum stress threshold for the given tooth, the minimum stress threshold comprising a minimum amount of stress required to cause the given tooth to move; obtaining a maximum stress threshold for the given tooth, the maximum stress threshold comprising a minimum amount of stress which would cause permanent damage to soft tissues around the given tooth; and determining the force as that which induces a stress in the given tooth between the minimum stress threshold and the maximum stress threshold.

In certain embodiments, the method further comprises determining one or both of the minimum stress threshold and the maximum stress threshold of the given tooth using a finite element analysis (FEA) method.

In certain embodiments, the predetermined threshold level is that which avoids inducing movement in the at least one other of the plurality of subject's teeth.

In certain embodiments, the predetermined threshold level is that which does not damage the at least one other of the plurality of subject's teeth or soft tissues surrounding the teeth.

In certain embodiments, the predetermined threshold level is that which can be countered by an orthodontic appliance to avoid movement of the at least one other of the plurality of subject's teeth.

In certain embodiments, the predetermined threshold level is determined based on a minimum stress threshold of a respective one of the other of the plurality of subject's teeth, and a maximum stress threshold of the respective one of the other of the plurality of subject's teeth, the minimum stress threshold comprising a minimum amount of stress required to cause the given respective tooth to move, and the maximum stress threshold comprising a minimum amount of stress which would cause permanent damage to soft tissues around the respective given tooth.

In certain embodiments, the method further comprises determining one or both of the minimum stress threshold and the maximum stress threshold of the given respective tooth using a finite element method on the given respective tooth.

In certain embodiments, the method further comprises displaying, on a display of the electronic device, the determined orthodontic treatment of the trajectory segment.

In certain embodiments, the method further comprises causing a manufacture of an orthodontic aligner according to the determined orthodontic treatment.

From a further aspect, there is provided a system for determining an orthodontic treatment for a tooth of a subject, the system comprising a processor of an electronic device, the processor being configured to execute a method comprising: acquiring a 3D digital model of an arch form of the subject, the 3D digital model of the arch form including representations of a plurality of the subject's teeth including a 3D digital model of the given tooth; identifying an initial tooth position of the given tooth; acquiring an indication of a target tooth position for the given tooth; obtaining a trajectory of the given tooth from the initial tooth position to the target tooth position, the trajectory comprising a plurality of trajectory segments; for a given segment of the plurality of trajectory segments, applying a force to the 3D digital model of the given tooth to displace the given tooth from a start position to an end position of the trajectory segment within a predetermined time interval, and determining an induced stress associated with at least one other of the plurality of subject's teeth; in response to a determination that the induced stress is above a threshold level, determining a counter force to be applied to the at least one other of the plurality of subject's teeth in order to counter the induced stress; determining, for the given segment, the orthodontic treatment as including the force to the given tooth and the counter force to the at least one other of the plurality of subject's teeth; and storing data indicative of the determined orthodontic treatment in a memory communicatively coupled to the processor.

According to another broad aspect of the present technology, there is provided a method for determining a tooth trajectory in orthodontic treatment for a tooth of a subject, the method being executable by a processor of an electronic device. The method comprises acquiring a 3D digital model of an arch form of the subject, the 3D digital model of the arch form including representations of a plurality of the subject's teeth including a 3D digital model of the given tooth; identifying an initial tooth position of the given tooth; acquiring an indication of a target tooth position for the given tooth; obtaining a preliminary trajectory of the given tooth from the initial tooth position to the target tooth position, the preliminary trajectory comprising a plurality of preliminary trajectory segments; and determining the tooth trajectory for the given tooth from the preliminary trajectory by executing an optimization algorithm on a first preliminary trajectory segment of the plurality of preliminary trajectory segments. The executing the optimization algorithm comprises applying a first preliminary force to the 3D digital model of the given tooth to displace the given tooth from a start position to an end position of the first preliminary trajectory segment within a predetermined time interval; determining a first induced stress associated with at least one other of the plurality of subject's teeth; in response to a determination that the first induced stress does not meet a threshold level, modulating the first preliminary force such that the first induced stress is modulated to a desirable level, thereby determining a first valid force to be applied to the given tooth; applying the first valid force to the given tooth at the start position of the first preliminary trajectory segment to determine a validated end position of the first preliminary trajectory segment, thereby defining a first validated trajectory segment; determining the tooth trajectory of the given tooth as including the first validated trajectory segment having the start position and the validated end position; using the determined tooth trajectory of the given tooth as part of the orthodontic treatment of the subject; and storing data indicative of the determined tooth trajectory or the orthodontic treatment in a memory communicatively coupled to the processor.

In certain embodiments, the method comprises determining the first preliminary force to be applied to the 3D digital model of the given tooth, the determining comprising: obtaining a minimum stress threshold for the given tooth, the minimum stress threshold comprising a minimum amount of stress required to cause the given tooth to move; obtaining an maximum stress threshold for the given tooth, the maximum stress threshold comprising a minimum amount of stress which would cause permanent damage to soft tissues around the given tooth; and determining the first preliminary force as being a force which would induce a stress in the given tooth between the minimum stress threshold and the maximum stress threshold.

In certain embodiments, the method further comprises determining one or both of the minimum stress threshold and the maximum stress threshold of the given tooth using a finite element analysis (FEA) method.

In certain embodiments, the desirable level of the first transfer force is that which avoids inducing movement in the at least one other of the plurality of subject's teeth.

In certain embodiments, the desirable level of the first transfer force is that which does not damage the at least one other of the plurality of subject's teeth or soft tissues surrounding the teeth.

In certain embodiments, the desirable level of the first transfer force is that which can be countered by an orthodontic appliance to avoid movement of the at least one other of the plurality of subject's teeth.

In certain embodiments, the desirable level of the first transfer force is determined based on a minimum stress threshold of a respective one of the other of the plurality of subject's teeth, and a maximum stress threshold of the respective one of the other of the plurality of subject's teeth, the minimum stress threshold comprising a minimum amount of stress required to cause the given respective tooth to move, and the maximum stress threshold comprising a minimum amount of stress which would cause permanent damage to soft tissues around the respective given tooth.

In certain embodiments, the method further comprises determining one or both of the minimum stress threshold and the maximum stress threshold of the given respective tooth using a finite element method on the given respective tooth.

In certain embodiments, the method further comprises determining a second validated trajectory segment, a start position of the second validated trajectory segment comprising the adjusted end position of the first validated trajectory segment, and an end position of the second validated trajectory segment being determined by applying a second preliminary force to the 3D digital model of the given tooth to displace the given tooth from the start position of the second validated trajectory segment to the end position of the second preliminary trajectory segment within a predetermined time interval; determining whether the application of the second preliminary force to the 3D digital model of the given tooth causes a second induced stress to be applied to at least one other of the plurality of subject's teeth; in response to a determination that the second induced stress does not meet a threshold level, modulating the second preliminary force such that the level of the second induced stress is modulated to a desirable level, thereby determining a second valid force to be applied to the given tooth; applying the second valid force to the given tooth at the start position of the second preliminary trajectory segment to determine an adjusted end position of the second preliminary trajectory segment, thereby defining the second validated trajectory segment.

In certain embodiments, the determining the preliminary trajectory of the given tooth from the initial tooth position to the target tooth position, comprises determining the plurality of preliminary trajectory segments so as to minimize a number of segments required to move the given tooth from the initial tooth position to the target tooth position.

In certain embodiments, the plurality of preliminary trajectory segments of the given tooth each has an equal distance interval or an equal time interval.

In certain embodiments, the method further comprises generating, by the optimization algorithm, respective tooth trajectories for other ones of the plurality of subject's teeth, the generating comprising determining a respective preliminary force to be applied to the 3D digital model of a respective tooth before determining the respective tooth trajectory, the determining comprising: obtaining a minimum stress threshold for the respective tooth, the minimum stress threshold comprising a minimum amount of stress required to cause the respective tooth to move; obtaining a maximum stress threshold for the respective tooth, the maximum stress threshold comprising a minimum amount of stress which would cause permanent damage to soft tissues around the respective tooth; and determining a respective preliminary force to be applied to the respective tooth and determining the respective preliminary force as being a force which would induce a stress in the respective tooth between the minimum stress threshold and the maximum stress threshold.

In certain embodiments, the method further comprises determining one or both of the minimum stress threshold value and the maximum stress threshold of the respective tooth using a finite element method.

In certain embodiments, the method further comprises displaying, on a display of the electronic device, the determined tooth trajectory or the planned orthodontic treatment of the given tooth.

In certain embodiments, the method further comprises displaying, on a display of the electronic device, the determined tooth trajectories or the planned orthodontic treatment of the other ones of the plurality of subject's teeth.

In certain embodiments, the method further comprises causing a manufacture of an orthodontic aligner according to the determined tooth trajectory or orthodontic treatment.

From another aspect, there is provided a system for determining a tooth trajectory in orthodontic treatment for a tooth of a subject, the system comprising a processor of an electronic device, the processor configured to execute a method. The method comprises acquiring a 3D digital model of an arch form of the subject, the 3D digital model of the arch form including representations of a plurality of the subject's teeth including a 3D digital model of the given tooth; identifying an initial tooth position of the given tooth; acquiring an indication of a target tooth position for the given tooth; obtaining a preliminary trajectory of the given tooth from the initial tooth position to the target tooth position, the preliminary trajectory comprising a plurality of preliminary trajectory segments; determining the tooth trajectory for the given tooth from the preliminary trajectory by executing an optimization algorithm on a first preliminary trajectory segment of the plurality of preliminary trajectory segments, the executing comprising applying a first preliminary force to the 3D digital model of the given tooth to displace the given tooth from a start position to an end position of the first preliminary trajectory segment within a predetermined time interval; determining whether the application of the first preliminary force to the 3D digital model of the given tooth causes a first induced stress associated with at least one other of the plurality of subject's teeth; in response to a determination that the first induced stress does not meet a threshold level, modulating the first preliminary force such that the first induced stress is modulated to a desirable level, thereby determining a first valid force to be applied to the given tooth; applying the first valid force to the given tooth at the start position of the first preliminary trajectory segment to determine an adjusted end position of the first preliminary trajectory segment, thereby defining a first validated trajectory segment; and determining the tooth trajectory of the given tooth as including the first validated trajectory segment having the start position and the validated end position; using the determined tooth trajectory of the given tooth as part of the orthodontic treatment of the subject; and storing data indicative of the determined tooth trajectory or the orthodontic treatment in a memory communicatively coupled to the processor.

In certain embodiments, the system further comprises a manufacturing system for manufacturing an orthodontic appliance for implementing the orthodontic treatment.

In the context of the present specification, unless expressly provided otherwise, the term "orthodontic treatment" is broadly referred to as any type of medical intervention aimed at correcting malocclusions associated with the teeth of the patient or moving the patient's teeth for any reason, including surgical and non-surgical manipulations, such as, but not limited to, using one or more of aligners, brackets, multi-strand wires, strips, retainers, and plates. Further, the orthodontic treatment, as referred to herein, may be determined automatically by a software, based on image data and other inputs associated with the subject, or semi-automatically with input from a practitioner such as an orthodontist, a maxillofacial surgeon, for example.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Certain aspects and embodiments of the present technology are directed to methods of and systems for developing at least a portion of an orthodontic treatment for a patient (also referred to herein as a "subject") which take into account certain safety and efficiency considerations. For the avoidance of doubt, "developing an orthodontic treatment" also encompasses validating, refining or optimizing a preliminary orthodontic treatment. The orthodontic treatment may comprise a number of successive treatment segments, each treatment segment defined by a respective trajectory segment representing movement of respective teeth within that treatment segment. Each treatment segment is associated with a predetermined treatment interval. In this respect, certain aspects and embodiments of the present technology are directed to methods of and systems for determining at least one trajectory segment of the orthodontic treatment.

More specifically, certain aspects and embodiments of the present technology include consideration of a force applied to a given tooth of the subject during the treatment segment, as well as transfer forces induced by the applied force on at least one other tooth of the patient. The transfer forces may induce movement in the other teeth or damage thereto.

For example, by implementing certain embodiments of the present technology to determine the tooth trajectory for the given tooth, it may be possible to determine an orthodontic treatment for the patient which is both safe and efficient. This can be achieved, in certain non-limiting embodiments of the present technology, by determining an optimized force to be applied to the given tooth which takes into account stress thresholds of tissues around the given tooth as well as stress thresholds of tissues around other teeth of the same arch form of the patient. Stress threshold considerations may include any one or more of: (a) avoiding or minimizing damage to the given tooth and tissues around the given tooth; (b) avoiding and/or minimizing damage to the other teeth and tissues of the same arch form of the patient; and (c) avoiding or mitigating induced movements of the other teeth through transfer forces from the force applied to the given tooth. Optimization may also take into account minimizing a duration of a given treatment segment, minimizing an overall duration of the orthodontic treatment, or minimizing a number of treatment segments whilst taking into account the above safety considerations.

Figure 1:
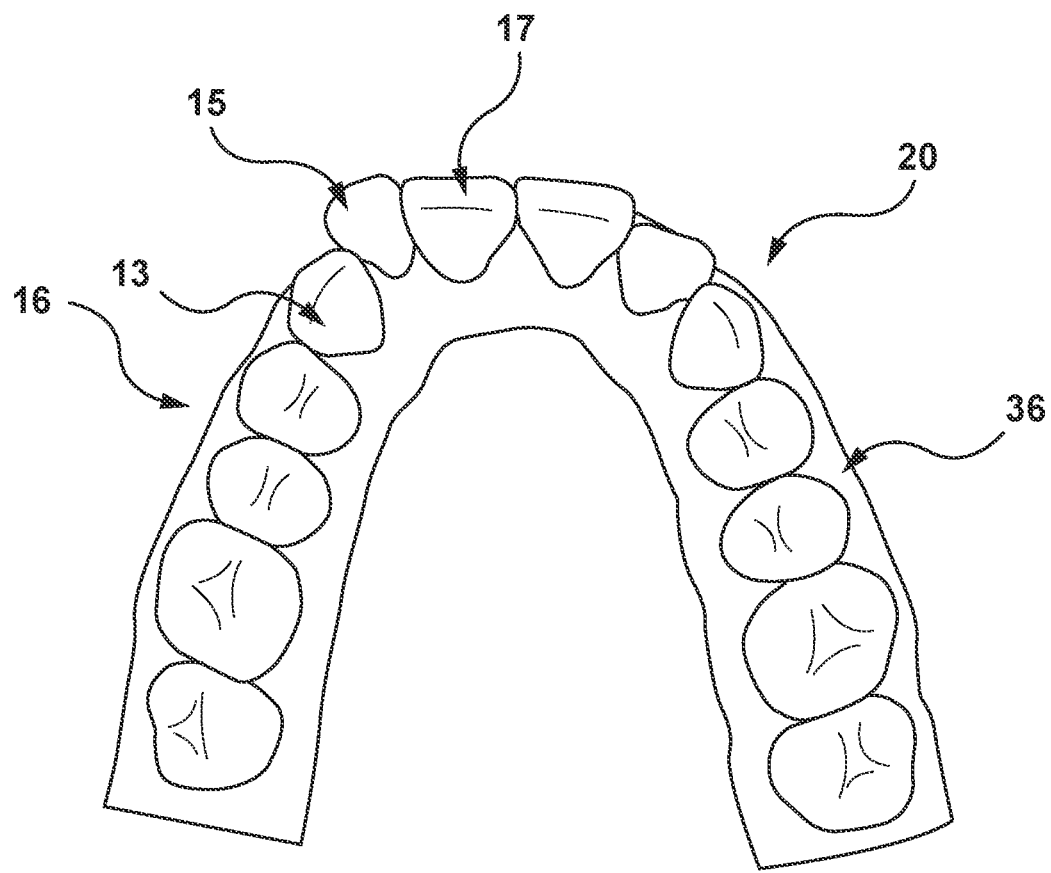
FIG. 1 depicts a bottom view of an upper arch form of a subject exemplifying a misalignment of some of subject's teeth, in accordance with certain non-limiting embodiments of the present technology.

Certain aspects and embodiments of the present technology will now be described below with reference to the upper teeth 16 of an upper arch form 20 of the subject (FIG. 1). However, it will be appreciated that embodiments of the present technology can be applied to any other teeth of any other arch form of the patient.

Orthodontic Appliances

Referring initially to FIG. 1, there is depicted a bottom view of the upper arch form 20 of the patient, to which certain aspects and non-limiting embodiments of the present technology may be applied.

As it can be appreciated, the upper arch form 20 includes the upper teeth 16 and upper gingiva 36. The upper teeth 16 include a tooth 15 which is misaligned, a first adjacent tooth 13 and a second adjacent tooth 17. As can be seen in FIG. 1, the tooth 15 is positioned outwardly relative to its neighboring teeth: the first adjacent tooth 13 and the second adjacent tooth 17. Thus, for the purposes of describing embodiments of the present technology, the orthodontic treatment to be determined for the patient is that of correcting the misalignment of the tooth 15, i.e. moving the tooth 15 from a start position shown in FIG. 1 to a target position in which the tooth 15 is aligned with its neighboring teeth.

In accordance with certain non-limiting embodiments of the present technology, the determined orthodontic treatment may comprise applying one or more orthodontic devices in the one or more treatment segments to the upper arch form 20. Generally speaking, the orthodontic device may be configured to exert a force onto the tooth 15 causing it to move towards the target position, that is, in the depicted embodiments of FIG. 1, inwardly between the first adjacent tooth 13 and the second adjacent tooth 17 to align with the first adjacent tooth 13 and the second adjacent tooth 17. The tooth 15 may be caused to move to the target position in one or more treatment segments. In various non-limiting embodiments of the present technology, the orthodontic device may comprise orthodontic appliances of different types, shapes, sizes and configurations, such as those including, without limitation, aligners, brackets, multi-strand wires, strips, retainers, and plates.

Figure 2A:
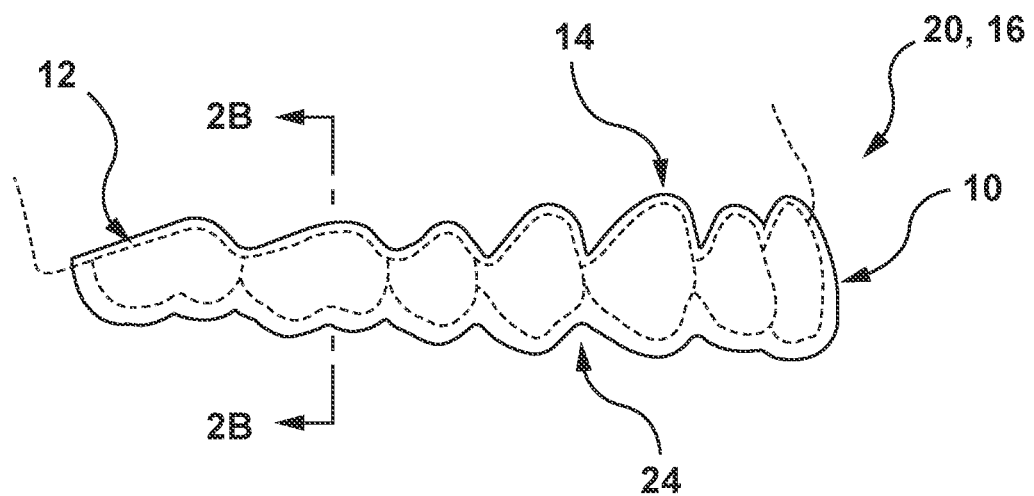
FIGS. 2A and 2B depict side and cross-sectional views, respectively, of a personalized dental appliance applied to subject's teeth that may be configured to treat the misalignment of the subject's teeth present in FIG. 1, in accordance with certain non-limiting embodiments of the present technology.
Figure 2B:
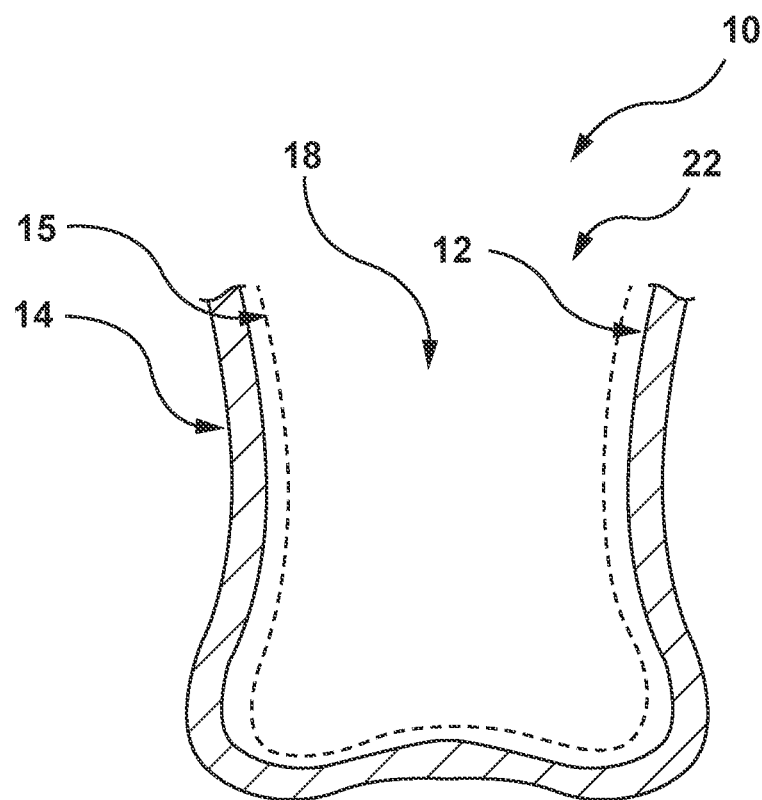

In specific non-limiting embodiments of the present the present technology, the orthodontic device may include an aligner. With reference to FIGS. 2A and 2B, there is depicted an aligner 10 applied to at least some of the upper teeth 16, in accordance with certain non-limiting embodiments of the present technology. The aligner 10 comprises an inner surface 12 and an outer surface 14. The inner surface 12 defines a channel 18, which is configured, in some non-limiting embodiments of the present technology, for receiving crown portions 26 (illustrated in FIGS. 3A and 3B) of at least some of the upper teeth 16 including the tooth 15, the first adjacent tooth 13, and the second adjacent tooth 17. However, in other non-limiting embodiments of the present technology, the channel 18 of the aligner 10 may be configured to receive crown portions 26 of all of the upper teeth 16. At least one edge of the channel 18 is shaped for following a gum line 22 along the upper gingiva 36.

In accordance with the non-limiting embodiments of the present technology, a size, a form factor (such as a U-shape or a V-shape, for example), and a configuration of the aligner 10, including a material and a thickness thereof, depend generally on a particular malocclusion disorder of the patient (such as the misalignment of the tooth 15 within the upper teeth 16) or the determined orthodontic treatment for the malocclusion. As an example, in some non-limiting embodiments of the present technology, the thickness of the aligner 10 may be about 0.7 mm. In other non-limiting embodiments of the present technology, the thickness is selected from 0.7 mm, 0.75 mm, 0.8 mm, 0.85 mm, 0.9 mm, 0.95 mm, and 1.0 mm. In yet other non-limiting embodiments of the present technology, the aligner 10 may have regions of variable thickness, such as in interdental regions 24 or occular regions, as an example.

According to certain non-limiting embodiments of the present technology, the aligner 10 may be made of a polymer, such as a thermoplastic material. In other non-limiting embodiments of the present technology, the aligner 10 may be made of poly-vinyl chloride (PVC). In yet other non-limiting embodiments of the present technology, the aligner 10 may be made of polyethylene terephthalate glycol (PETG). Other suitable materials can also be used to form the aligner 10.

It is to be appreciated that, in accordance with certain non-limiting embodiments of the present technology, the aligner 10 may be used for treating different types of teeth misalignment or malocclusion, including but not limited to one or more of: closing gaps ("space closure"), creating/widening gaps, tooth rotation, tooth intrusion/extrusion, and tooth translation, to name a few. It should further be noted that in certain non-limiting embodiments of the present technology, applying the aligner 10 to the upper teeth 16 may further include applying specific attachments (also known as "fixing blocks") thereto.

The aligner 10 is configured in such a way that its inner surface 12 imposes contacts to impose a desired force on one or more of the upper teeth 16 to obtain the target position of the one or more upper teeth 16 at a given stage of the orthodontic treatment.

Needles to say, that although in the depicted embodiments of FIGS. 2A and 2B the aligner 10 is configured to be applied to the upper teeth 16, in other non-limiting embodiments of the present technology, the aligner 10 may be configured to be applied to teeth of a lower arch form of the patient.

Orthodontic Treatment

Efficiency Considerations

In order to cause the tooth 15 to reach the target position, the determined orthodontic treatment may comprise a number of sequential treatment steps in which a number of different aligners 10 are applied to the teeth 16. Sequential treatment steps may be required to move different teeth at different times to achieve respective target positions (e.g. by avoiding collisions or by creating space for other teeth to move into), to sub-divide a trajectory of a given tooth into intervals to stay within safety limitations, to sub-divide a trajectory of a given tooth to avoid collisions or to create space.

Thus, referring back to FIG. 1 and for the specific configuration of the teeth 16 shown in FIG. 1, in order to cause the tooth 15 to reach the target position, the determined orthodontic treatment may comprise sequential treatment steps in which different aligners 10 are sequentially applied to the teeth 16. For example, in the sequential treatment steps, the upper teeth 16, other than the tooth 15, may be first moved to create a space around the tooth 15, and then the tooth 15 caused to move inwardly into the space towards the target position within the upper teeth 16.

In determining the orthodontic treatment and more specifically a given trajectory of the given tooth, certain embodiments of the present technology may take into account an efficiency of orthodontic treatment. By efficiently is meant either in as few sequential orthodontic treatment steps to achieve the target position, or as short a time as possible from starting the orthodontic treatment to attaining the target position. The efficiency of the orthodontic treatment may increase the chances of the patient's adherence to the orthodontic treatment and hence its success and can also minimize certain costs associated with the orthodontic treatment. However, efficiency must be considered alongside safety.

Safety Considerations

Figure 3B:
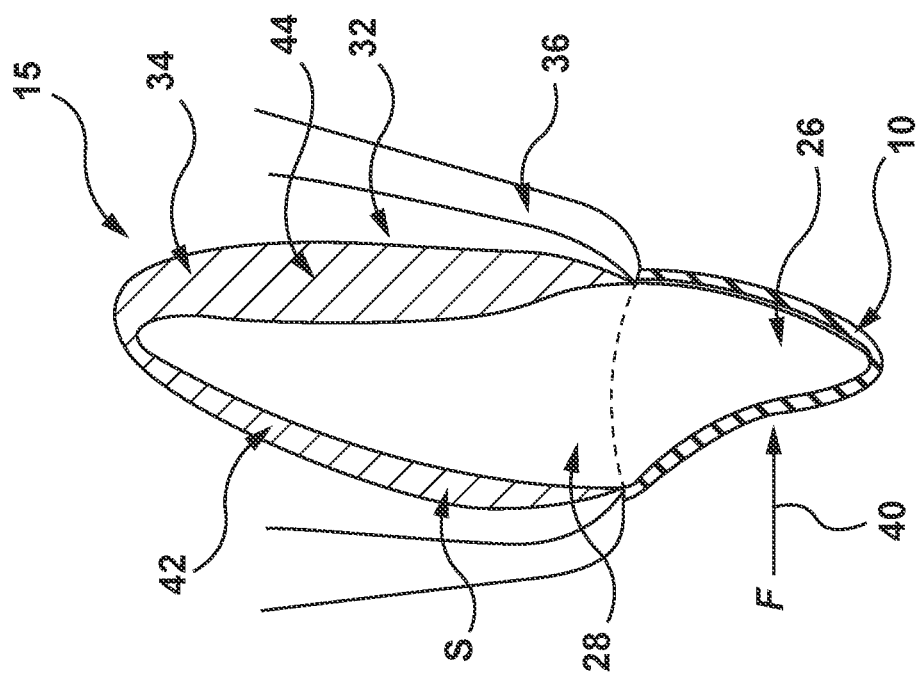
FIGS. 3A and 3B schematically depict internal anatomy of a given one of the subject's teeth present in FIG. 1 with and without application of the personalized dental appliance of FIGS. 2A and 2B, respectively, in accordance with certain non-limiting embodiments of the present technology.

Biomechanical processes allowing a given one of the upper teeth 16 to move in the course of the orthodontic treatment, such as the tooth 15 towards the target position, under the respective force imposed by the aligner 10 will now be described with reference to FIGS. 3A and 3B.

Figure 3A:
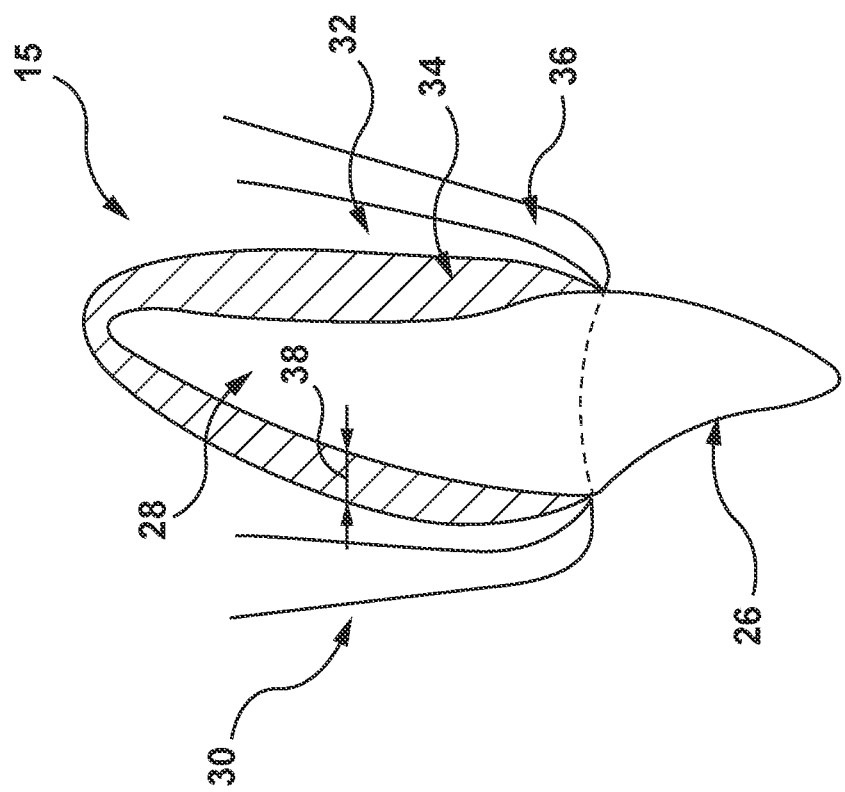

FIG. 3A depicts a cross-sectional view of the tooth 15 schematically illustrating some surrounding tissues thereof, in accordance with certain non-limiting embodiments of the present technology. As the tooth 15 is on the upper arch form 20, the crown portion is depicted as extending downwardly. FIG. 3B depicts the same cross-sectional view of the tooth 15 under a force 40 exerted by the aligner 10 (the aligner 10 is omitted for clarity).

The tooth 15 includes the crown portion 26 and a root portion 28. Tissues of a periodontium 30 surrounding and supporting the tooth 15 include the upper gingiva 36, an alveolar bone 32, and a periodontal ligament (PDL) 34. The PDL 34 surrounds the root portion 28 and attaches the tooth 15 to the alveolar bone 32. As it can be appreciated from FIG. 3B, the aligner 10 causes the force 40 to be applied to the crown portion 26 of the tooth 15, which may cause the tooth 15 to pitch, causing compression of the PDL 34 on a compressed portion 42 of the root portion 28, and tension of the PDL 34 on a strained portion 44 of the root portion 28. Resultant remodelling of the alveolar bone 32 surrounding the tooth 15, with bone resorption of the alveolar bone 32 occurring on the compressed portion 42, and bone deposition of the alveolar bone 32 on the strained portion 44, causes the tooth 15 to be displaced.

The force 40 directly applied to the tooth 15 by the aligner 10 can be defined by force parameters such one or more of: a magnitude of the directly applied force 40, a duration of the directly applied force 40, a direction of the force 40, a surface area on the tooth 15 to which the force 40 is applied, and a position on the crown portion 26 of the tooth 15 to which the force is applied. The force 40 may also be defined in terms of induced stresses in the PDL 34, for example, an induced stress in the PDL 34 of the tooth 15 to which the force 40 is being applied.

The PDL 34 of the tooth 15 can be considered as having a minimum stress threshold, below which the tooth 15 will not move. Therefore, for the tooth 15 to move, the induced stress in the PDL 34 must be above the minimum stress threshold. A magnitude of the minimum stress threshold of the PDL 34 may be associated with certain parameters of the applied force 40 to the tooth. Furthermore, the minimum stress threshold of PDLs 34 of different teeth may vary from one another. Different teeth with differing surface area likely have a different volume of periodontal ligament.

The PDL 34 of the tooth 15 can also be considered as having a maximum stress threshold, beyond which the PDL 34 or other tissues of the periodontium 30 will be damaged. The maximum stress threshold of the PDL 34 may be associated with certain parameters of the force 40 applied to the tooth 15. The damage may include resorption of the root portion 28; necrosis in the upper gingiva 36 through excess compression of proximal blood vessels and nerve pathways; damage to the PDL; pain; pulpal changes; periodontal disease such as gingivitis, loss of the alveolar bone 32, periodontitis, and the like, to name a few.

Developers have appreciated that certain forces 40 which are applied may also result in induced stresses in the PDLs of other teeth (i.e. other than the tooth 15) through the force 40 applied to the given tooth being transferred to other teeth of the same arch form. Such transferred forces are herein referred to as "transfer forces".

The induced stresses in the PDLs 34 of the other teeth are associated with certain parameters of the force 40 applied to the tooth 15 as well as relative configuration of the other teeth to the tooth 15 to which the force is being applied. For example, the tooth 13 and the tooth 17 may have higher induced stresses, induced from the force 40 being applied to the tooth 15, than other teeth 16 of the arch form which are further from the tooth 15. Also, higher induced stresses of the tooth 13 and the tooth 17 may be obtained with a force 40 of higher magnitude.

In certain embodiments, a potential consequence of the transfer force is unintentional or undesired tooth movements for certain teeth for which the induced stress in their respective PDLs 34 exceeds the minimum stress threshold.

Figure 4:
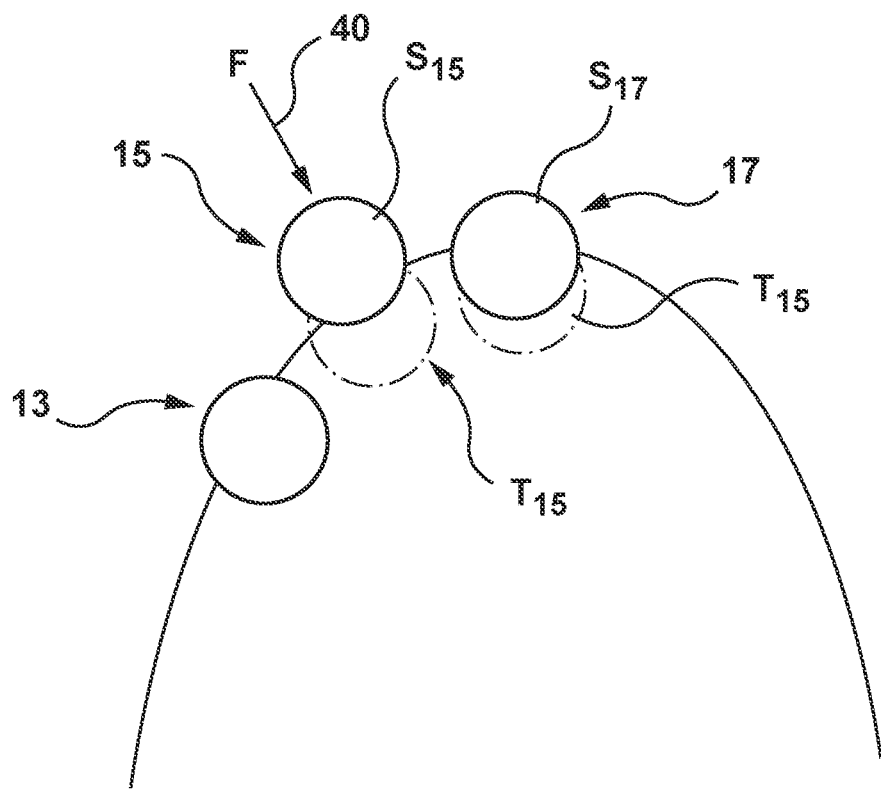
FIG. 4 depicts a schematic diagram of the upper arch form of FIG. 1 and showing the misaligned tooth and adjacent teeth, in accordance with certain embodiments of the present technology.

For example, and with reference to FIG. 4, there is shown a plan view of the upper arch form 20 of FIG. 1 showing the tooth 13, the tooth 15 and the tooth 17, and with all other upper teeth 16 omitted for clarity. Applying the force 40 to the tooth 15 causes an induced stress in the PDL 34 of the tooth 15 which is greater than the minimum stress threshold of the PDL 34 causing the tooth 15 to move from the start position $S_{15}$ towards the target position $T_{15}$. The applied force 40 also induces transfer forces to the tooth 13 and the tooth 17. The transfer forces induce a stress in the PDL 34 of the tooth 17 which is higher than its minimum stress threshold thereby also causing the tooth 17 to move from the start position $S_{17}$ to the position $T_{17}$. However, the transfer forces induce a stress in the PDL 34 of the tooth 13 which is lower than its minimum stress threshold thereby the tooth 13 is not affected.

Therefore, according to certain embodiments of the present technology, in determining the orthodontic treatment and hence the configuration of the aligner 10, embodiments of the present technology take into account such transfer forces.

Thus, non-limiting embodiments of the present technology described herein are directed to determining a tooth trajectory of a given tooth within a given treatment segment (referred to herein as a "trajectory segment") which optimizes the force 40 applied to it by the orthodontic appliance and takes into account the above safety considerations, and particularly transfer forces on at least some of the teeth of the same arch form other than the given tooth, and as well as, optionally, an efficiency of the orthodontic treatment.

How the trajectory segment is thus determined, and how it may be used for planning the orthodontic treatment, according to certain non-limiting embodiments of the present technology, will be described with reference to systems and methods described below and with reference to FIGS. 5 to 13.

System

Figure 5:
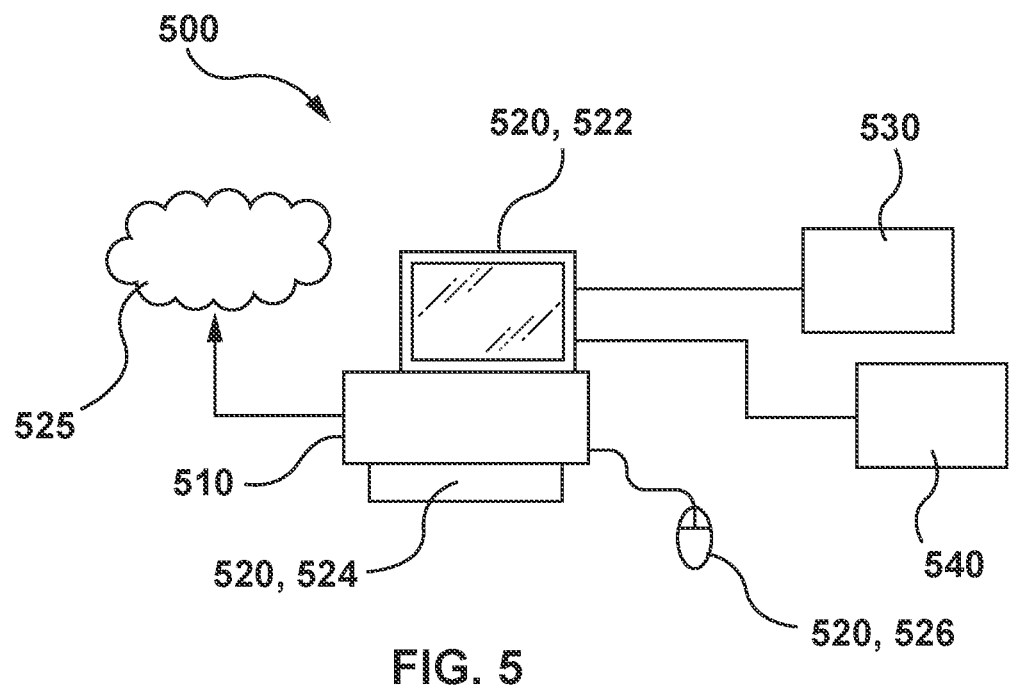
FIG. 5 depicts a schematic diagram of a system for planning an orthodontic treatment, in accordance with certain embodiments of the present technology.
Figure 6:
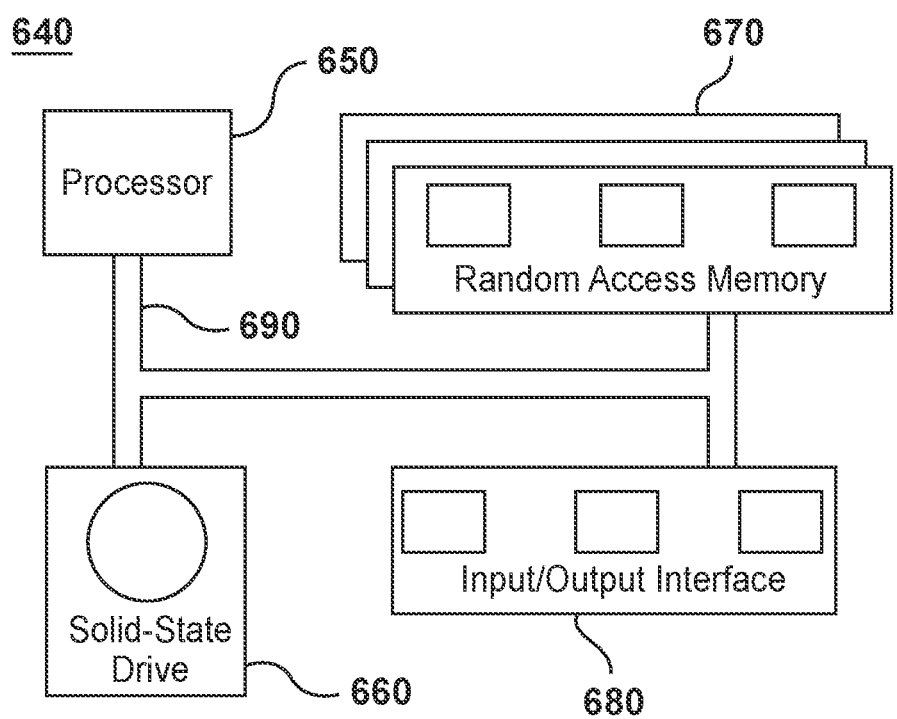
FIG. 6 depicts a schematic diagram of a computing environment of the system of FIG. 5, in accordance with certain embodiments of the present technology.

Referring to FIGS. 5 and 6, there is depicted a schematic diagram of a system 500 suitable for determining the tooth trajectory of a given tooth, such as the tooth 15, for planning the orthodontic treatment, in accordance with certain non-limiting embodiments of the present technology.

It is to be expressly understood that the system 500 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 500 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 500 may provide in certain instances simple implementations of the present technology, and that where such is the case they have been presented in this manner as an aid to understanding. As persons skilled in the art would further understand, various implementations of the present technology may be of a greater complexity.

Broadly the system 500 of FIG. 5 comprises a computer system 510 having at least one interface device 520 for providing an input or an output to a user of the system 500. The system may further comprise an imaging device 530 communicatively coupled to the computer system 510, and optionally a manufacturing system 540 for making an orthodontic appliance, such as the aligner 10.

Computer System

In certain non-limiting embodiments of the present technology, the computer system 510 may be configured, by pre-stored program instructions, to generate, based on image data associated with the patient, the orthodontic treatment for the patient. More specifically, the computer system 510 may be configured to determine at least one of a number of successive treatment segments, each treatment segment defined by trajectory segments representing movement of respective teeth within that treatment segment.

To that end, in some non-limiting embodiments of the present technology, the computer system 510 is configured to receive image data pertaining to the patient or to a given stage of the orthodontic treatment. According to some non-limiting embodiments of the present technology, the computer system 510 may receive the image data via local input/output interface (such as USB, as an example, not separately depicted). In other non-limiting embodiments of the present technology, the computer system 510 may be configured to receive the image data over a communication network 525, to which the computer system 510 is communicatively coupled.

In some non-limiting embodiments of the present technology, the communication network 525 is the Internet and/or an Intranet. Multiple embodiments of the communication network may be envisioned and will become apparent to the person skilled in the art of the present technology. Further, how a communication link between the computer system 510 and the communication network 525 is implemented will depend, inter alia, on how the computer system 510 is implemented, and may include, but is not limited to, a wire-based communication link and a wireless communication link (such as a Wi-Fi communication network link, a 3G/4G communication network link, and the like).

It should be noted that the computer system 510 can be configured for receiving the image data from a vast range of devices. Some of such devices can be used for capturing and/or processing data pertaining to maxillofacial and/or cranial anatomy of the patient. In certain embodiments, the image data received from such devices is indicative of properties of anatomical structures of the patient, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

In alternative non-limiting embodiments of the present technology, the computer system 510 may be configured to receive the image data associated with the patient directly from the imaging device 530 communicatively coupled thereto.

Imaging Device

Broadly speaking the imaging device 530 may be configured to capture and/or process the image data of the upper teeth 16 and the periodontium (not depicted) of the patient. In certain non-limiting embodiments of the present technology, the image data may include, for example, one or more of: (1) images of external surfaces of respective crown portions (such as the crown portion 26 of the tooth 15) of the upper teeth 16, (2) images of an external surface of the periodontium including those of the upper gingiva (not depicted), the alveolar maxillary bone (not depicted), and images of superficial blood vessels and nerve pathways associated with the upper teeth 16; and (3) images of an oral region. By doing so, the imaging device 530 may be configured, for example, to capture image data of the upper arch form 20 of the patient. In another example, the imaging device may also be configured to capture and/or process image data of a lower arch form associated with the patient without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 530 may comprise an intra-oral scanner enabling to capture direct optical impressions of the upper arch form 20 of the patient.

In a specific non-limiting example, the intraoral scanner can be of one of the types available from MEDIT, corp. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 530 may comprise a desktop scanner enabling to digitize a mold representing the upper arch form 20. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from Dental Wings, Inc. of 2251, ave Letourneux, Montreal (QC), Canada, H1V 2N9. It should be expressly understood that the desktop scanner can be implemented in any other suitable equipment.

In yet other non-limiting embodiments of the present technology, the imaging device 530 may comprise a cone beam computed tomography (CBCT) scanner. Generally speaking, the CBCT scanner comprises software and hardware allowing for capturing data using a cone-shaped X-ray beam by rotating around the patient's head. This data may be used to reconstruct 3D representations of the following regions of the patient's anatomy: dental (teeth and gum, for example); oral and maxillofacial region (mouth, jaws, and neck); and ears, nose, and throat ("ENT").

In a specific non-limiting example, the CBCT scanner can be of one of the types available from 3Shape, Private Limited Company of Holmens Kanal 7, 1060 Copenhagen, Denmark. It should be expressly understood that the CBCT scanner can be implemented in any other suitable equipment.

Further, it is contemplated that the computer system 510 may be configured for processing of the received image data. The resulting image data of the upper arch form 20 received by the computer system 510 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 510 may further comprise a corresponding computing environment.

Computing Environment

With reference to FIG. 6, there is depicted a schematic diagram of a computing environment 640 suitable for use with some implementations of the present technology. The computing environment 640 comprises various hardware components including one or more single or multi-core processors collectively represented by the processor 650, a solid-state drive 660, a random-access memory 670 and an input/output interface 680. Communication between the various components of the computing environment 640 may be enabled by one or more internal and/or external buses 690 (e.g. a PCI bus, universal serial bus, IEEE 1394 "Firewire" bus, SCSI bus, Serial-ATA bus, ARINC bus, etc.), to which the various hardware components are electronically coupled.

The input/output interface 680 allows enabling networking capabilities such as wire or wireless access. As an example, the input/output interface 680 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 680 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 660 stores program instructions suitable for being loaded into the random-access memory 670 and executed by the processor 650, according to certain aspects and embodiments of the present technology. For example, the program instructions may be part of a library or an application.

In some non-limiting embodiments of the present technology, the computing environment 640 is implemented in a generic computer system, which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 640 can be implemented may be envisioned without departing from the scope of the present technology.

Interface Device

Referring back to FIG. 5, the computer system 510 has the at least one interface device 520 for providing an input or an output to a user of the system 500, the interface device 520 being in communication with the input/output interface 680. In the embodiment of FIG. 5, the interface device 520 is a screen 552. In other non-limiting embodiments of the present technology, the interface device 520 may be a monitor, a speaker, a printer or any other device for providing an output in any form such as an image form, a written form, a printed form, a verbal form, a 3D digital model form, or the like.

In the depicted embodiments of FIG. 5, the interface device 520 also comprises a keyboard 524 and a mouse 526 for receiving input from the user of the system 500. Other interface devices 520 for providing an input to the computer system 510 can include, without limitation, a USB port, a microphone, a camera or the like.

The computer system 510 may be connected to other users, such as through their respective clinics, through a server (not depicted). The computer system 510 may also be connected to stock management or client software which could be updated with stock when the orthodontic treatment has been determined and/or schedule appointments or follow-ups with clients, for example.

Manufacturing System

The system 500 could, in some embodiments, further include the manufacturing system 540 for making the aligner 10, operatively communicable with the computer system 510. While described as being generally co-located with other portions of the system 500, it is also contemplated that the manufacturing system 540 could be disposed at a separate location and be communicatively connected to remaining portions of the system 500 as described above, such as by an internet connection. In some such implementations, the computer system 510 could send manufacturing instructions to the manufacturing system 540, for example. Details relating to the manufacturing system and processes implemented therewith will be described briefly herein. Further information can be found in U.S. Pat. No. 10,717,208, entitled "METHODS AND SYSTEMS FOR THERMOFORMING ORTHODONTIC ALIGNERS", issued on Jul. 21, 2020, the entirety of which is incorporated herein by reference.

In certain embodiments, the manufacturing system 540 includes a thermoforming device for shaping a precursor aligner into the aligner 10 using an aligner mold and a precursor aligner. The thermoforming device is configured to receive the aligner mold and the precursor aligner, and to shape the precursor aligner onto the aligner mold during a thermoforming operation, in which heat and pressure imparted to the precursor aligner during shaping are controlled.

In some embodiments, the manufacturing system 540 further includes a computer-assisted post-processing device such as a computer numerical control (CNC) milling device or a CNC laser cutting device for further shaping the aligner 10 into a post-processed aligner (not shown). The post-processing of the aligner 10 may include one or both of (i) forming recesses or openings in the aligner body, and (ii) forming an edge of the channel 18. In some such embodiments, the post-processing device is operatively connectable to the computer system 510 for receiving operating instructions from the computer system 510 for post-processing the aligner 10. The operating instructions may for example be derived from a digital model indicative of a desired aligner (not shown).

In some embodiments, the manufacturing system 540 further includes an auxiliary manufacturing device for making the aligner mold. The auxiliary manufacturing device is an additive manufacturing device, also referred to in some cases as a 3-D printing device. It is also contemplated that, in other embodiments, a CNC milling device may be used instead. In certain embodiments, an auxiliary manufacturing device may be used for making precursor aligners, for example an additive manufacturing device arranged for fabricating customized precursor aligners.

In some embodiments, the computer system 510 is configured to receive image data from the imaging device 530 pertaining to the patient or to a given orthodontic treatment (such as a digital model of the aligner 10). The computer system 510 may use the image data for determining the thermoforming parameters. In certain embodiments, the computer system 510 is arranged to determine an orthodontic treatment using the image data.

In certain non-limiting embodiments, the system 500 further includes a robotic system arranged relative to the thermoforming device, for handling one or more of the aligner mold, the precursor aligner, and the aligner 10. In some non-limiting embodiments, the robotic system could be omitted.

In certain embodiments, the system 500 and/or computer system 510 could be connectable to one or more of the imaging device 530, the thermoforming device, the post-processing device, the auxiliary manufacturing device and the robotic system (where included) via a communication network. In some embodiments, the communication network is the Internet and/or an Intranet. Multiple embodiments of the communication network may be envisioned and would be apparent to the person skilled in the art of the present technology.

Orthodontic Treatment Planning

As previously alluded to, according to the non-limiting embodiments of the present technology, the processor 650 may be configured to: (1) receive the image data associated with the patient's teeth, such as the upper teeth 16; (2) based on the received image data, determine, for at least some of the upper teeth 16, a respective tooth trajectory, for example, the tooth trajectory of the tooth 15 which respects certain safety considerations of at least some of the upper teeth 16; (3) based on the so determined tooth trajectory, determine the orthodontic treatment for the patient; and one or more of (4i) cause the manufacture of an orthodontic appliance for applying the orthodontic treatment, such as the aligner 10, (4ii) cause the display of the determined orthodontic treatment, and (4iii) save the determined orthodontic treatment.

3D Digital Models

According to some non-limiting embodiments of the present technology, having received the image data, the processor 650 may be configured to generate 3D digital models of one or more arch forms of the patient. Alternatively, the processor 650 may be configured to receive the 3D digital models of the one or more arch forms of the patient, such as from the imaging device 530 or from the memory.

Figure 7:
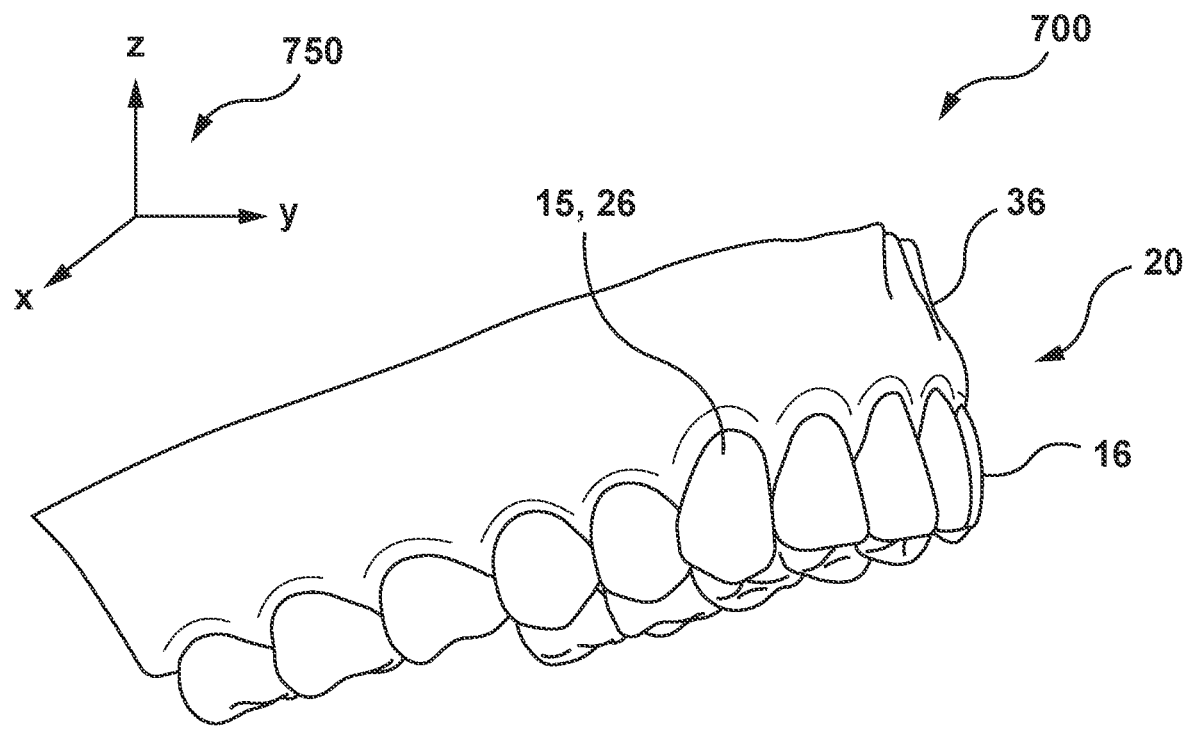
FIG. 7 depicts a perspective view of a 3D digital model of the upper arch form of FIG. 1, in accordance with the non-limiting embodiments of the present technology.

With reference to FIG. 7, there is depicted a perspective view of a 3D digital model 700 representing a configuration of the upper arch form 20 of the patient prior to applying the orthodontic treatment, in accordance with the non-limiting embodiments of the present technology.

More specifically, the 3D digital model 700 of the upper arch form 20 depicts a representation of outer surfaces of the upper teeth 16 and the upper gingiva 36. As it can be appreciated, the upper teeth 16 are represented, in the 3D digital model 700, by respective crown portions associated therewith, such as the crown portion 26 of the tooth 15.

The 3D digital model 700 may have any appropriate format such as a mesh, point cloud, etc. In certain embodiments, the 3D digital model 700 of the upper arch form 20 comprises a plurality of mesh elements (not depicted) representative of a surface of the upper arch form 20. The plurality of mesh elements may include, without limitation, triangular mesh elements, quadrilateral mesh elements, convex polygonal mesh elements, or even concave polygonal mesh elements, as an example, without departing from the scope of the present technology.

The 3D digital model 700 may include a coordinate system 750 associated with the 3D digital model 700. In one non-limiting example, the processor 650 may be configured to determine the coordinate system 750 such that an XY plane thereof is parallel to a transverse plane associated with a patient's skull (not depicted). In another example, the XY plane may be parallel to a Frankfort horizontal plane associated with the patient's cranium (not depicted).

In some non-limiting embodiments of the present technology, the processor 650 may be configured to cause segmentation of the 3D digital model 700 of the upper arch form 20 in order to determine boundaries between crown portions of adjacent teeth, and/or boundaries between a given tooth and a surrounding gingiva, thereby generating a plurality of so isolated crown portions associated with at least one tooth of the upper arch form 20.

To that end, according to some non-limiting embodiments of the present technology, the processor 650 may be configured to apply one or more approaches to automatic tooth segmentation, for example, that which is described in a co-owned U.S. Pat. No. 10,695,147-B1, entitled "METHOD AND SYSTEM FOR DENTAL BOUNDARY DETERMINATION", issued Jun. 30, 2020; the content of which is hereby incorporated by reference in its entirety.

How the processor 650 can be configured to isolate the crown portion is not limited; and, in some non-limiting embodiments of the present technology, the processor 650 can be configured to apply, to the 3D digital model 700, one or more automatic tooth segmentation approaches described in a co-owned U.S. Pat. No. 10,888,397-B1 issued on Jan. 12, 2021, entitled "METHOD AND SYSTEM FOR DENTAL BOUNDARY DETERMINATION", content of which is incorporated herein by reference in its entirety.

Further, in some non-limiting embodiments of the present technology, using the so generated segmented crown portions associated with the at least one tooth of the upper arch form 20, the processor 650 may further be configured to model tooth movements of at least some of the upper teeth 16 of the upper arch form 20 to determine the orthodontic treatment.

In additional non-limiting embodiments of the present technology, for a more effective modeling of the movements of the given tooth, such as the tooth 15, by applying respective forces thereto (such as the force 40), the processor 650 may be configured to augment the 3D digital model 700, such as the crown portion 26 of the tooth 15 separated from surrounding gingiva 36. Augmenting the 3D digital model 700 may include one or more of: (1) augmenting the 3D digital model of the crown portion 26 with a reconstructed 3D digital model of the root portion 28 (for example, in those embodiments where the imaging device 530 is the intra-oral scanner used for generating the 3D digital model 700 and which does not capture any image data pertaining to the root portion 28); (2) augmenting the 3D digital model 700 of the crown portion 26 with a reconstructed surface to remove artefacts; and (3) augmenting the 3D digital model 700 of the arch form 20 with a reconstructed gingival surface to remove artefacts.

To that end, according to certain non-limiting embodiments of the present technology, the processor 650 may be configured to apply certain tooth reconstruction techniques described in a co-owned U.S. Pat. No. 11,026,767-B1, issued on Jun. 8, 2021 and entitled "SYSTEMS AND METHODS FOR PLANNING AN ORTHODONTIC TREATMENT", the content of which is incorporated hereby by reference in its entirety.

Figure 8:
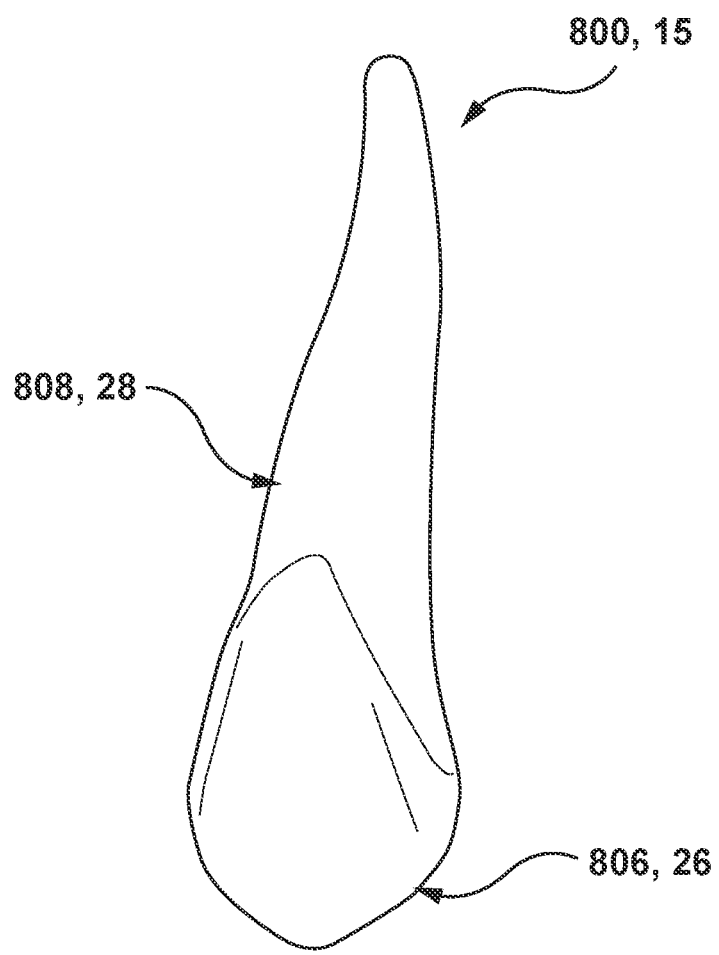
FIG. 8 depicts a 3D digital model of the given one of the subject's teeth of FIGS. 3A and 3B used, by the processor of FIG. 6, to implement a method of the present technology, in accordance with the non-limiting embodiments of the present technology.

FIG. 8 depicts a tooth 3D digital model 800 of the tooth 15 derived from the 3D digital model 700 of FIG. 7, in accordance with certain non-limiting embodiments of the present technology. The tooth 3D digital model 800 includes a crown 3D representation 806 of the crown portion 26 and optionally a root 3D representation 808 of the root portion 28. The tooth 3D digital model 800 may have been generated by the processor 650 or obtained by other means. The processor 650 may have generated the tooth 3D digital model 800 based on the methods described above and incorporated by reference herein, or in any other manner.

The processor 650 may be configured to use the tooth 3D digital model 800 for one or more of: modelling forces applied to the tooth 15, determining stress thresholds of the tooth 15, and determining the transfer forces of the other teeth.

Determining Stress Thresholds

In accordance with certain non-limiting embodiments of the present technology, the processor 650 may be configured to determine the stress thresholds associated with the tooth 15, as well as the other teeth of the upper arch form 20. In other embodiments, the processor 650 may be configured to obtain the stress thresholds from a memory of a computer system, such as the memory 670.

Referring back to FIGS. 3A and 3B, in the context of the present specification, the term "stress thresholds" includes one or more of a minimum stress threshold, a maximum stress threshold, and an optimal stress threshold. The minimum stress threshold denotes a minimum amount of stress that must be applied to the tissues of the periodontium 30 of the given tooth, such as the tooth 15 or the other teeth 16 of the arch form 20, to cause the given tooth to move.

At the minimum stress threshold, the PDL 34 may start the process of bone remodeling. Stresses that occur less than the minimum stress threshold are perceived as normal load on the given tooth and when such stresses occur, restructuring of bone tissue does not occur. Any tooth movement occurring due to induced stresses lower than the minimum stress threshold may be considered reversible.

The maximum stress threshold denotes a maximum amount of stress that can be applied to the tissues of the periodontium 30 of the given tooth, such as the tooth 15 or the other teeth 16 of the arch form 20, before causing possibly irreversible damage to the periodontium 30. For example, bone tissue restructuring at these high stresses may be irreversible and PDL 34 recovery may not be possible or require long recovery times.

The optimal stress threshold denotes an optimal amount of stress that can be applied to the tissues of the periodontium 30 of the given tooth, such as the tooth 15 or the other teeth 16 of the arch form 20, at which bone restructuring occurs but without damage to the PDL 34.

According to certain non-limiting embodiments of the present technology, the processor 650 may be configured to determine the stress thresholds associated with the teeth 16, such as the tooth 15, the tooth 13 and the tooth 17. The processor may 650 may also be configured to determine associated forces to be applied to the teeth based on the stress thresholds.

In certain embodiments, the processor 650 is configured to determine the stress thresholds based on a Stress Cumulative Distribution Function (SCDF). In some non-limiting embodiments of the present technology, the SCDF may be predetermined for each of the upper teeth 16, such as the tooth 15, empirically, based on analyzing deformation features of the periodontium 30 under various external forces. Further, in specific non-limiting embodiments of the present technology, the analyzing the deformation forces may include analyzing a finite element model of the tooth 15, which the processor 650 may be configured to generate based on the tooth 3D digital model 800. Broadly speaking, in these embodiments, the SCDF may be configured to return a portion of a surface of the PDL 34, where stress is greater than an amount of stress of interest caused by a given external force. Thus, according to certain non-limiting embodiments of the present technology, the SCDF may be formalized by the following equation:

$$\text{SCDF}(F_i, s_i) = S_i(\text{PDL}), \qquad (1)$$

where $F_i$ is an external force (e.g. the force 40 applied to the tooth 15);

$s_i$ is a respective amount of stress caused by the external force $F_i$; and $S_i(\text{PDL})$ is a portion of the surface of the PDL 34 influenced by a greater amount of stress than $s_i$.

Figure 9:
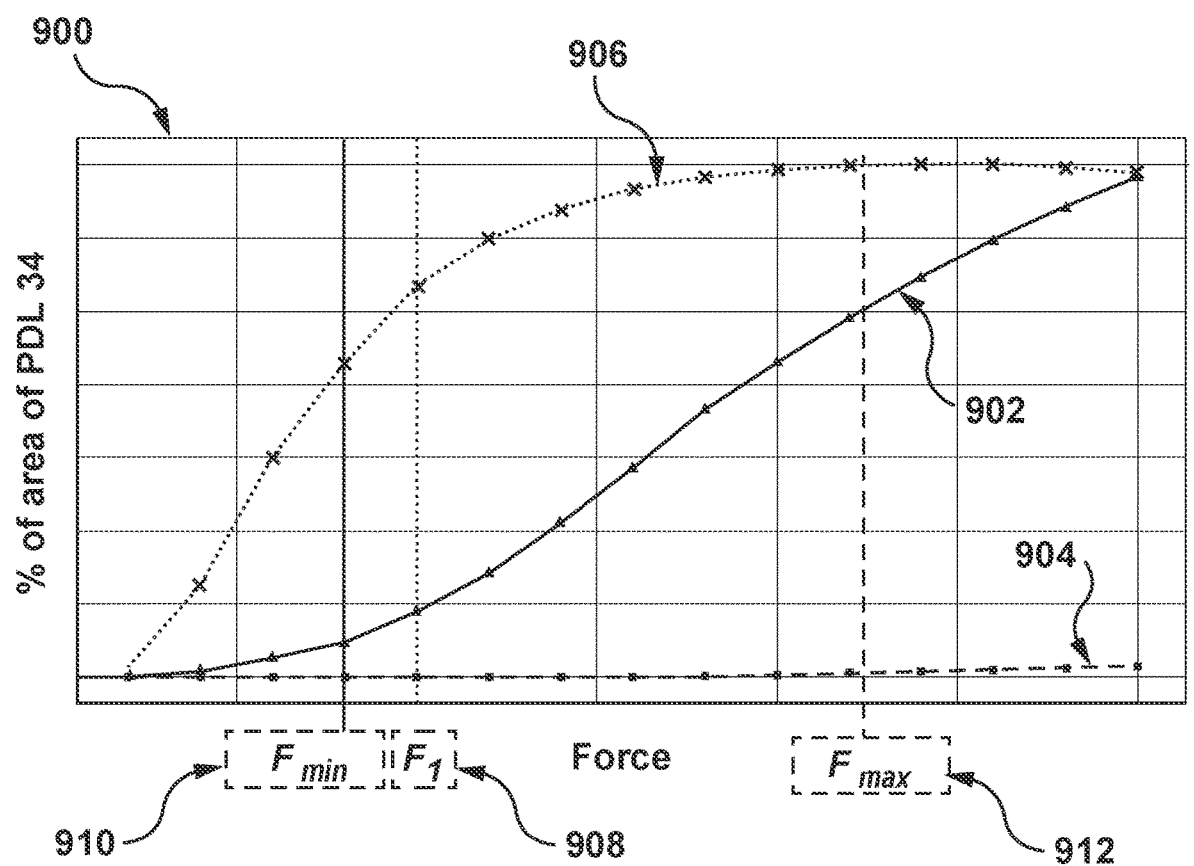
FIG. 9 depicts an example stress nephogram applied, by the processor of FIG. 6, to determine stress thresholds for at least some of the subject's teeth of FIG. 1 and to implement a method of the present technology, in accordance with certain non-limiting embodiments of the present technology.

With reference to FIG. 9, there is provided a stress nephogram 900 having been generated by the processor 650, for the tooth 15 based on analyzing the tooth 3D digital model 800, in accordance with certain non-limiting embodiments of the present technology. Alternatively, the processor 650 may retrieve the stress nephogram 900 from a memory such as the memory 670.

According to certain non-limiting embodiments of the present technology, the stress nephogram 900 is indicative of stress distribution within the PDL 34 under influence of various external forces defining the SCDF for the tooth 15. More specifically, the stress nephogram 900 shows a behaviour of stress distributed within a respective portion of the PDL 34 (indicated by the vertical axis in the stress nephogram 900) caused by a respective external force (indicated by the horizontal axis in the stress nephogram 900). Additionally or alternatively, the stress nephogram 900 may include data indicative of strain distribution within the PDL 34 under respective external forces.

Thus, in certain non-limiting embodiments of the present technology, the stress nephogram 900 may include an indication of (1) an admissible stress distribution curve 902 indicating a distribution of admissible stress, which does not cause permanent damage to the PDL 34, and thus may cause the tooth 15 either to move or rest within the upper arch form 20; (2) a dangerous stress distribution curve 904 indicating a distribution of dangerous stress, which, when applied to the PDL 34, may cause permanent damage thereof; and (3) an admissible strain distribution curve 906 indicating distribution of admissible strain within the PDL 34.

For example, according to the stress nephogram 900, a given force 908, $F_1$, applied to the tooth 15 may cause an admissible amount of stress to, approximately, 9% of a surface of the PDL 34; an admissible amount strain to around 53% of the surface of the PDL 34, and no dangerous stress to the PDL 34. Thus, in this example, SCDF ($F_1$, $s_1$)=0.

Thus, according to certain non-limiting embodiments of the present technology, the processor 650 may be configured to identify forces relating to the stress thresholds including: (i) a minimum force 910, $F_{min}$, corresponding to the minimum stress threshold applied to the PDL 34 causing the tooth 15 to move, and (ii) a maximum force 912, $F_{max}$, corresponding to an amount of stress beyond which permanent damage to the PDL 34 may be caused. Thus, based on the stress nephogram 900, the processor 650 may be configured to identify the following sets of forces:

1) the set of admissible forces applicable to the PDL 34 without causing the permanent damage thereto:

$$F^{adm}: \text{SCDF}(F_i, s^{max}) \sim 0, \text{ further including:} \quad (2)$$

2) a set of forces causing the tooth 15 to rest:

$$F^{rest}: \text{SCDF}(F_i, s^{min}) \sim 0, \text{ and} \quad (3)$$

3) a set of drive forces causing the tooth 15 to move in a respective direction associated with a each force therefrom:

$$F^{drive}: \{\text{SCDF}(F_i, s^{max}) \sim 0 \ \text{SCDF}(F_i, s^{min}) > 0 \Rightarrow F^{drive} \in [F_{min}^{drive}, F_{max}^{drive}]. \quad (4)$$

Accordingly, as it may become apparent from the above, any force beyond the set of admissible forces $F^{adm}$ may cause the permanent damage to the PDL 34 of the tooth 15.

Thus, the processor 650 may be configured to determine, based on a respective tooth 3D representation, a respective range of stress thresholds for each modelled movement (such as translation, rotation, controlled/uncontrolled tipping, or extrusion/intrusion, for example) of each one of the upper teeth 16 for further determining a respective valid force therefrom.

As mentioned earlier, the processor 650 may be configured to use the set of admissible forces $F^{adm}$ to determine the respective valid force to be applied to the tooth 15, in the course of the orthodontic treatment.

Figure 10:
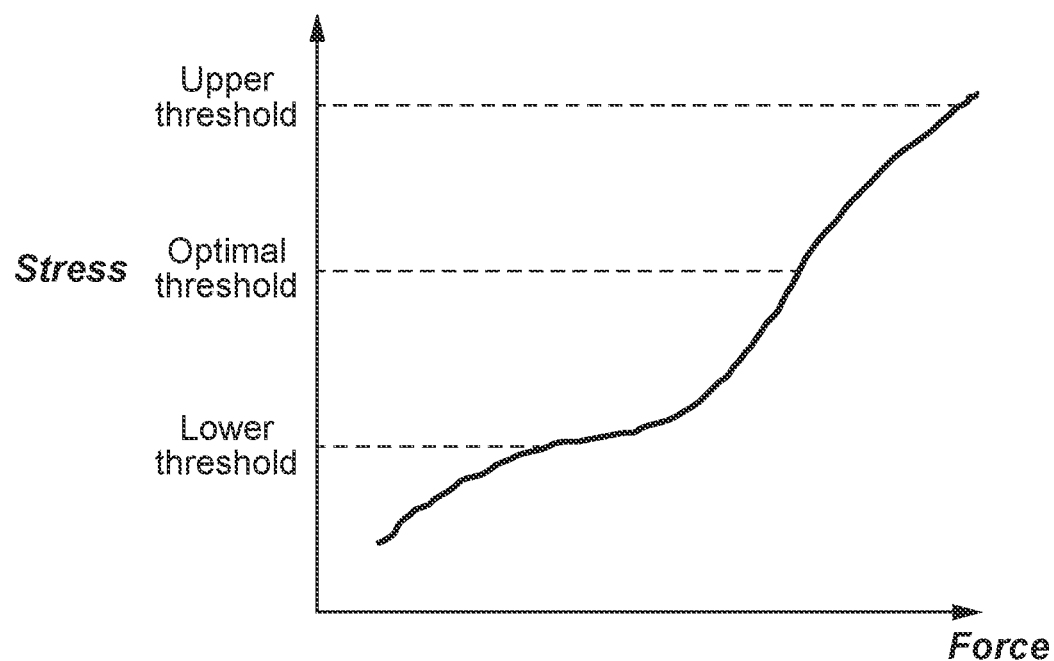
FIG. 10 depicts a schematic graph illustrating a relationship between stress thresholds associated with a tooth, such as one of the teeth of FIG. 1, and force applied to the given tooth, in accordance with certain non-limiting embodiments of the present technology.

Referring now to FIG. 10 which depicts the induced stresses by the force 40 applied in the PDL 34 of the tooth 15 with the stress thresholds marked thereon: minimum stress threshold, maximum stress threshold and optimal stress threshold. The thresholds were derived for each tooth using finite element analysis. The area and magnitude of stress occurring in the periodontal ligament was analyzed.

Figure 11:
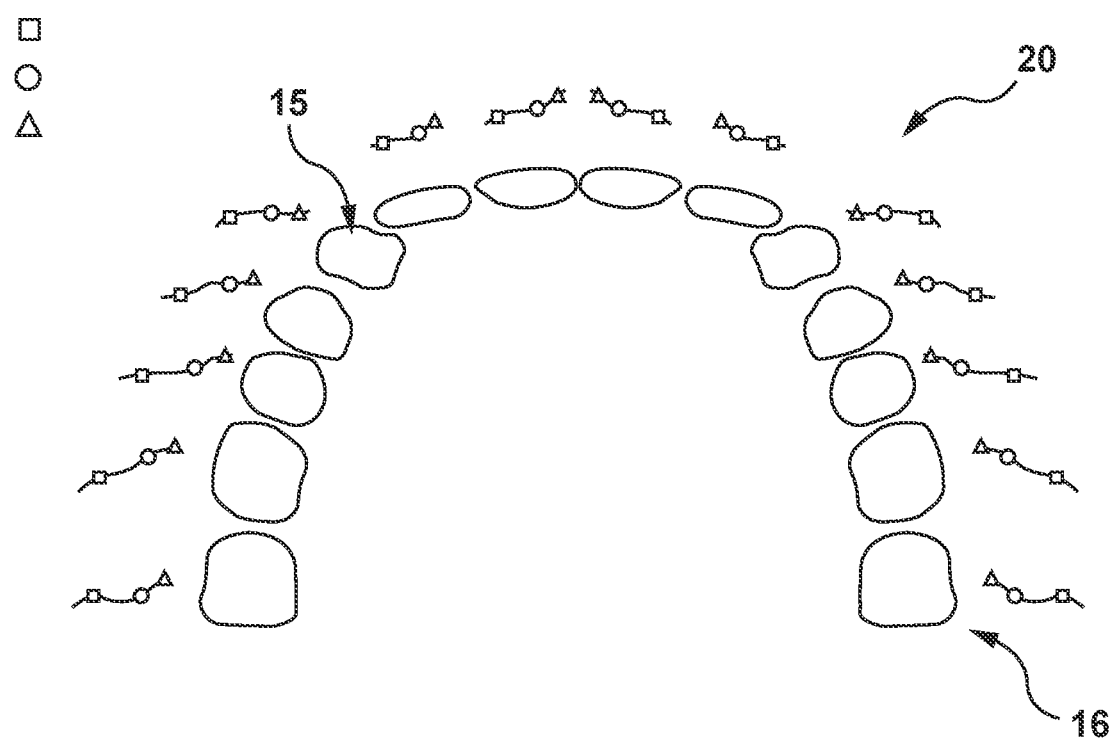
FIG. 11 depicts a schematic illustration of the teeth of the upper arch form of FIG. 1 with the associated stress thresholds indicated, in accordance with certain non-limiting embodiments of the present technology.

In the above manner, stress thresholds for a plurality of the upper teeth 16 may thus be determined, an example of which is illustrated in FIG. 11.

Determining Transfer Forces

As noted hereinabove, force applied to the given tooth, such as the tooth 15 under the force 40 may cause application of transfer forces to at least some of the other teeth of the arch form 20.

According to certain non-limiting embodiments of the present technology, to determine the transfer forces, the processor 650 may be configured to apply a Displacement Response Force Distribution Function (DRFDF). According to certain non-limiting embodiments of the present technology, the DRFDF may be constructed based on a superposition property of the forces caused by a displacement of a given tooth 3D representation within the 3D digital model 700. Thus, for example, the additional forces caused by the application of the force 40 applied to the 3D digital model 700 may be determined in accordance with the following equation:

$$F_{1 \ldots n} = \text{DRFDF}_1 \times \vec{d}_1, \quad (7)$$

where $F_{1 \ldots n}$ is a vector of the transfer forces applied, in the respective treatment segment, to respective tooth 3D representations involved in the orthodontic treatment in response to applying the force 40 causing the first displacement of the tooth 15 $\vec{d}_1$; and $\text{DRFDF}_1$ is a matrix of coefficients indicative of force magnitude values of the transfer forces associated with the applying the force 40.

According to certain non-limiting embodiments of the present technology, the $\text{DRFDF}_1$ may have dimensions of (6n×6), where n is a number of the respective teeth involved in the orthodontic treatment using the aligner 10, and the dimension 6 corresponds to 6 DOF of each of the respective teeth, to which a respective one of the transfer forces propagates.

According to certain non-limiting embodiments of the present technology, the $\text{DRFDF}_1$ may be populated, for example, based on finite element analysis of the respective teeth 3D digital models, their associated PDLs (such as the PDL 34 associated with the 3D digital model 700 of the tooth 15) with respective configurations of the aligner 10 applied thereto.

Accordingly, in additional non-limiting embodiments of the present technology, where the transfer forces are caused by respective displacements of more than one tooth within the 3D digital model 700, the processor 650 may be configured to determine them in accordance with the following equation:

$$F_{1 \ldots n} = \Sigma_j (\text{DRFDF}_j \times \vec{d}_j). \quad (8)$$

Thus, based on the applying the DRFDF, the processor 650 may be configured to determine the transfer forces $F_{1 \ldots n}$ including their magnitudes and directions satisfying the following constraints as described above in above in respect of Equations (2) to (4):

$F_j \in F_j^{adm}$—an admissible stress constraint;

$F_j \in F_j^{drive}$—forces used to cause a given tooth 3D representation to move in directions associated therewith; and $F_j \in F_j^{rest}$—forces used to cause the given tooth 3D representation to rest.

It should be expressly understood that the above list of constraints applied to the transfer forces $F_{1 \ldots n}$ is not exhaustive, and in additional non-limiting embodiments of the present technology, may further include constraints for a respective minimum stress threshold of each of the additional forces $F_{1 \ldots n}$—for example, corresponding to the lower threshold (causing a given tooth to rest, $F_j^{rest}$). Such constraints may be used to allow for proper reformation of a PDL of a respective one of the upper teeth 16.

Thus, according to certain non-limiting embodiments of the present technology, based on the DRFDF as defined by Equations (7) and (8), the processor 650 may be configured to determine each displacement of the respective tooth 3D representations within the 3D digital model 700, in the treatment segment, caused by the transfer forces applied thereto in response to, at least, the applied force 40.

Tooth Trajectory and Segments

As mentioned above, the orthodontic treatment may be defined at least in part by determining a trajectory segment of a given tooth with a given treatment segment, such as the tooth 15 moving from the start position $S_{15}$ to the target position $T_{15}$ (FIG. 4). The trajectory segment may be achieved over a plurality of treatment segments in which the tooth 15 is moved by a determined distance through application of a determined force, such as a "valid force", which takes into safety requirements of at least one other tooth of the arch form 20.

Thus, in certain embodiments, the processor 650 may be configured to determine at least one trajectory segment of the orthodontic treatment, the trajectory segment being indicative of a portion of the trajectory of the given tooth from the start position to the target position. In certain embodiments, the processor 650 is configured to determine all the trajectory segments defining the trajectory from the start position to the target position.

Figure 12A:
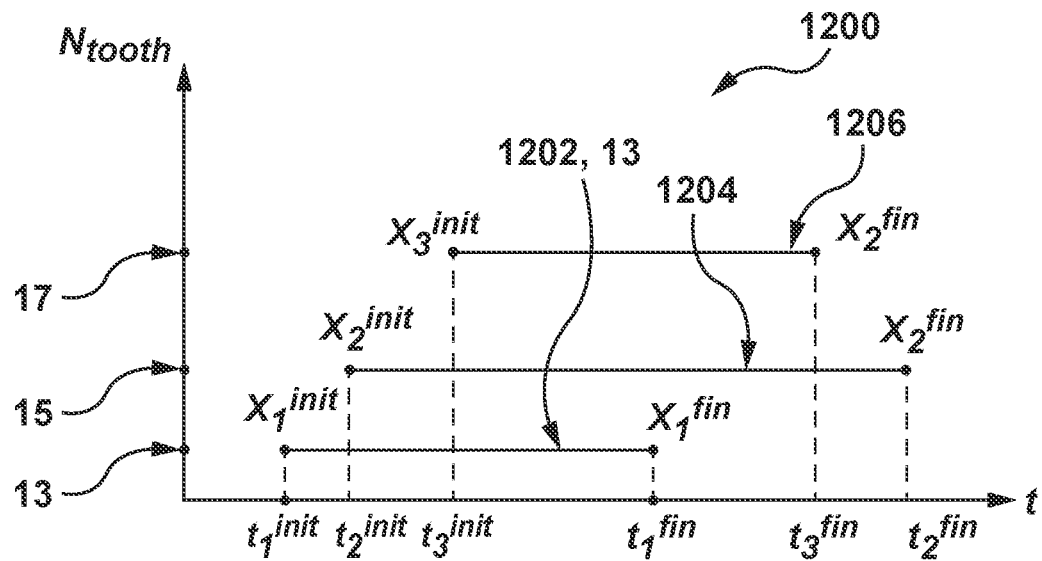
FIG. 12A depicts a schematic diagram of example preliminary and validated tooth trajectories for the misaligned tooth of FIG. 1 and the two adjacent teeth, determined by the processor of FIG. 6, in accordance with certain non-limiting embodiments of the present technology.

Referring to FIG. 12A, there is provided a schematic diagram of an example schedule 1200 determined by the processor 650 of trajectories of some of the upper teeth 16, such as the tooth 15, the first adjacent tooth 13, and the second adjacent tooth 17, in accordance with certain non-limiting embodiments of the present technology.

As it can be appreciated from the schedule 1200, each one of a first trajectory 1202, a second trajectory 1204, and a third trajectory 1206 defining movements of the first adjacent tooth 13, the tooth 15, and the second adjacent tooth 17, respectively, is associated with at least two moments in time: (1) an initial moment in time $t_j^{init}$ associated with a respective initial position of the tooth 15 ($X_2^{init}$), the first adjacent tooth 13 ($X_1^{init}$), and the second adjacent tooth 17 ($X_3^{init}$) within the upper arch form 20, which, for example, may be representative of the current configuration of the these teeth as depicted in FIG. 1; and (2) a final moment in time $t_j^{fin}$ associated with a respective target position of the tooth 15 ($X_2^{fin}$), the first adjacent tooth 13 ($X_1^{fin}$), and the second adjacent tooth 17 ($X_3^{fin}$), such as that being indicative of alignment of the tooth 15. FIG. 12A indicates that the tooth 15 may continue to be displaced after the tooth 13 and the tooth 15 have reached their target positions, the tooth 13 and the tooth 17 having been moved to make space for the tooth 15.

According to certain embodiments of the present embodiment, present methods and systems can also determine the schedule of the different trajectory segments of the trajectory. The processor 650 may perform this, in certain embodiments, by optimizing preliminary trajectory segments of the trajectory. The preliminary trajectory segments may be determined by the processor 650 in any applicable manner, such as by dividing the trajectory into trajectory segments of equal time, or applying a predetermined time per trajectory segment to the trajectory. The preliminary trajectory segments may also have been determined through a validation process performed by the processor 650, or another processor, such as collision detection.

Figure 12B:
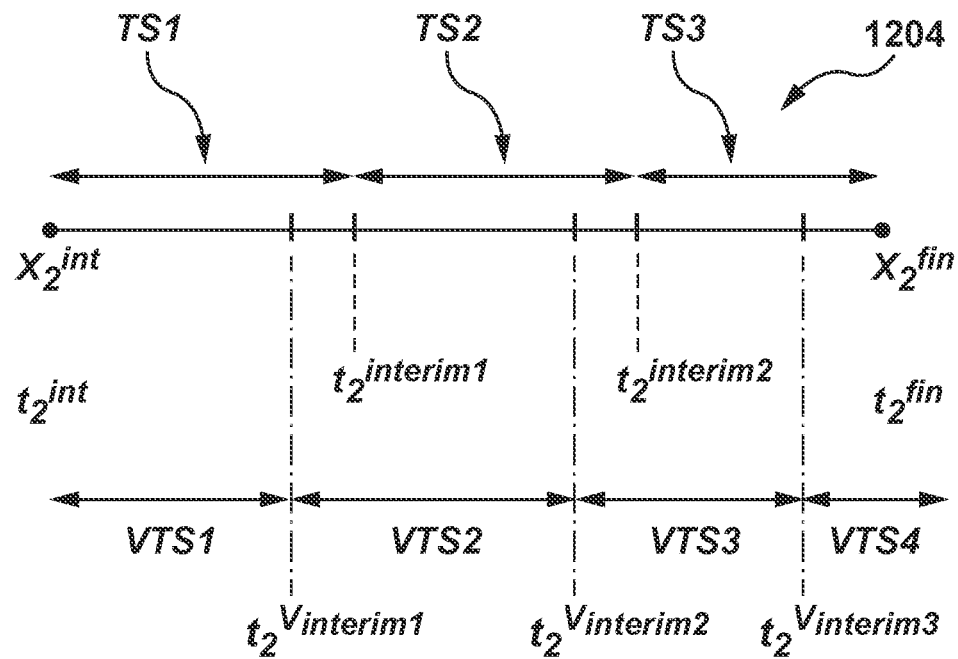
FIG. 12B depicts a schematic diagram of the tooth trajectory of FIG. 12A for the misaligned tooth of FIG. 1, the trajectory being sub-divided into preliminary trajectory segments, in accordance with certain non-limiting embodiments of the present technology.

FIG. 12B depicts the second trajectory 1204 of the tooth 15 in which the trajectory 1204 has been sub-divided into three preliminary trajectory segments, TS1, TS2 and TS3. $t_2^{interim1}$ indicates the end time of the first trajectory segment TS1 and start of the second trajectory segment TS2, and $t_2^{interm2}$ indicates the end of the second trajectory segment TS2 and the start of the third and final trajectory segment TS3. It will be appreciated that each trajectory segment may be associated with different movement distances and/or directions of the tooth 15, and hence different applied aligners 10 in each treatment segment. Each end and start time of the given tooth has an associated position of the tooth in the arch form 20.

An example of the optimized preliminary trajectory segments is also depicted in FIG. 12B as validated trajectory segments VTS1, VTS2, VTS3 and VTS4. As can be seen, in certain embodiments, the validated trajectory segments may be modulated versions of the preliminary trajectory segments, in terms of time (i.e. duration of each trajectory segment) and/or number (i.e. number of trajectory segments within the trajectory of the given tooth). In other embodiments, the validated trajectory segments may at least partially remain the same as the preliminary trajectory segments. In the example of FIG. 12B, the validated trajectory segment VTS1 has a validated end time which is different than the end time of the preliminary trajectory segment TS1. The validated end time will be the validated start time of the second validated trajectory segment VTS2. It will be appreciated that each validated end time of the given tooth will have an associated position in the arch form 20 at the end of the validated trajectory segment. Similarly, each validated start time of the given tooth will have an associated position in the arch form 20 at the start of the validated trajectory segment.

Accordingly, for determining at least one of the first trajectory 1202, the second trajectory 1204, and the third trajectory 1206 including their respective validated trajectory segments, in certain non-limiting embodiments of the present technology, the processor 650 may be configured to determine or obtain, based on the 3D digital model 700 or a derivative thereof, the respective initial positions of at least one of the tooth 15, the first adjacent tooth 13, and the second adjacent tooth 17 within the coordinate system 750 associated with the 3D digital model 700. In other words, the processor 650 may be configured to determine 6 degrees of freedom (DOF) of at least one of the tooth 15, the first adjacent tooth 13, and the second adjacent tooth 17 at a given initial moment in time $t_j^{init}$, to thereby identify the start position (e.g. $S_{15}$, $S_{17}$) thereof within the upper arch form 20.

Further, according to certain non-limiting embodiments of the present technology, the processor 650 may be configured to determine or obtain, based on the 3D digital model 700 or a derivative thereof, the respective target positions $X_j^{fin}$ of at least one of the tooth 15, the first adjacent tooth 13, and the second adjacent tooth 17 within the coordinate system 750 associated with the 3D digital model 700. In other words, the processor 650 may be configured to acquire 6 degrees of freedom (DOF) within the coordinate system 750 of the respective target position, of at least one of the tooth 15, the first adjacent tooth 13, and the second adjacent tooth 17, for example Tis in FIG. 4. In some non-limiting embodiments of the present technology, the respective target position for each of the teeth may be provided by the clinician. In other non-limiting embodiments of the present technology, the processor 650 may be configured to determine the respective target positions based on averaged data associated with aligned teeth received from a group of patients.

According to certain embodiments of the present technology, the processor 650 may be configured to determine the validated trajectory segments by optimizing, by the processor 650, a preliminary force applied to a given tooth of the tooth 3D digital model 800 at a respective initial moment in time $t_2^{init}$.

The optimization, which will be described in further detail below, may be based on the stress thresholds with the purpose of avoiding one or more of: a damage to the tissues of the periodontium 30 of the tooth 15; a damage to the tissues of the periodontium 30 of the other teeth 16; and unintended tooth movement in the arch form 20.

Following the determination of the valid force to be applied to the tooth 15, the processor 650 may then be configured, in certain embodiments, to use the valid force to determine the validated trajectory segment by applying the validated force to the given tooth at the start position of the preliminary trajectory segment. Thus, according to certain non-limiting embodiments of the present technology, by applying the valid force to the tooth 3D digital model 800 of the given tooth, a respective displacement of the given tooth may be modelled to thereby determine the validated end position thereof. The validated trajectory segment thus is considered to have the start position and the validated end position.

The processor 650 may then determine the orthodontic treatment as including the validated trajectory segment. The validated trajectory segment or the determined orthodontic treatment may be stored by the processor 650, such as in a memory of the computing system.

In certain embodiments, the processor 650 may also be configured to determine other validated trajectory segments of the given trajectory, by assuming for example that the validated end position of a prior trajectory segment is equivalent to the validated start position of a next trajectory segment. In this manner, the processor 650 may be configured to determine all the validated trajectory segments of a given trajectory for a given tooth. The processor 650 may also be configured to repeat this process for other teeth 16 of the arch form 20.

According to certain embodiments of the present technology, the processor 650 is configured to apply one or more validation processes to the one or more validated trajectory segments or to the one or more preliminary trajectory segments. One example of a validation process is collision detection in which it is determined whether the relative movement of the teeth within a treatment segment may give rise to collisions between the teeth. Any suitable method can be used by the processor 650 for collision detection such as that described in a co-owned U.S. Pat. No. 10,993,782-B1, entitled "SYSTEMS AND METHODS FOR DETERMINING A TOOTH TRAJECTORY", issued on May 4, 2021; the content of which is hereby incorporated by reference in its entirety; and as described in a co-owned U.S. Pat. No. 10,695,146-B1 entitled "SYSTEMS AND METHODS FOR DETERMINING ORTHODONTIC TREATMENTS", issued on Jun. 30, 2020; the content of which is hereby incorporated by reference in its entirety.

Once the validated trajectory segments of a given treatment segment are obtained, the processor 650 may be configured to determine the orthodontic appliance to apply to the teeth in that given treatment segment based on the determined valid forces to be applied to the teeth.

In certain embodiments, the processor 650 is configured to cause a manufacture of the so determined orthodontic appliance, such as the aligner 10, by sending instructions to a manufacturing system such as the manufacturing system 540.

Optimization

Turning now to the optimization applied by the processor 650 to determine the valid force and hence the validated trajectory segment. The optimization will be described with reference to determining the validated trajectory segment VTS1 for the tooth 15 in the trajectory 1204 (FIG. 12B). As noted above, embodiments of the present technology take into consideration the preliminary force applied to the tooth 3D digital model 800 of the tooth 15 at the initial moment in time $t_2^{init}$ to displace the tooth 15 to an end position of the preliminary trajectory segment, such as a position associated with $t_2^{termin1}$.

In certain embodiments, the preliminary force may be based on an arbitrary value that is selected or obtained by the processor 650. The arbitrary value may be a predetermined force value. In such a case, the preliminary force may be determined as the force required to move the given tooth along the predetermined tooth movement distance in a given segment treatment time or for the predetermined segment treatment time.

It should be noted that as the preliminary force is arbitrary it may violate a safety requirement. This may be confounded by the preliminary trajectory segment in certain embodiments also being somewhat arbitrary. For example, the preliminary force when applied to the tooth 15 may cause one or more of: a damage to the tissues of the periodontium 30 of the tooth 15; a damage to the tissues of the periodontium 30 of the other teeth 16; and unintended tooth movement in the arch form 20. For example, applying the preliminary force to the tooth 15 in order to move only the tooth 15 may cause movement of the tooth 13 or the tooth 17 (as depicted in FIG. 4, for example).

The optimization is, in certain embodiments, based on the transfer forces related to the preliminary force applied to the tooth 15. As noted above, transfer forces are related to stresses induced in PDLs or other tissues associated with the other teeth of the arch form (i.e. other than the tooth to which the force was applied). Stress thresholds, as mentioned above, may be defined in certain embodiments of the present technology as being the minimum stress threshold below which the given tooth does not move, the maximum stress threshold above which damage in incurred, and the optimal stress threshold in which movement of the tooth is induced without damage.

The processor 650 is thus configured to determine an induced stress or transfer force associated with at least one other of the upper teeth 16 of the upper arch form 20, such as in the manner described herein, and responsive to the determined induced stress, determine whether to modulate the preliminary force. If modulation is required, the processor may be configured to modulate the preliminary force to a desirable level.

The determination of whether and how to modulate the preliminary force depends on for example one or both of: avoiding damage to the tissues of the periodontium 30 of the tooth 15; avoiding damage to the tissues of the periodontium 30 of the other teeth 16 of the upper arch form 20; avoiding and unintended tooth movement of the other teeth 16 in the upper arch form 20; and not meeting a desired movement of the other teeth 16 in the upper arch form 20. If the induced stress is found not to meet a threshold level, the preliminary force may be modulated until a desired stress level is met.

In one example, in order to avoid or minimize damage to the tissues of the periodontium 30 of the other teeth 16 of the upper arch form 20, the processor 650 may determine the valid force as being lower than the preliminary force if the determined induced stress is above the maximum stress threshold for the given other tooth. For example if the induced stress of the tooth 13 or the tooth 17 is above the maximum stress threshold, the processor 650 may be configured to lower the preliminary force.

In another example, in order to avoid or minimize unintended tooth movement of the other teeth 16 in the upper arch form 20, the processor 650 may determine the valid force as being lower than the preliminary force if the determined induced stress is above the minimum stress threshold for the given other tooth (but below the maximum stress threshold). For example if the induced stress of the tooth 13 or the tooth 17 is above the minimum stress threshold but below the maximum stress threshold, the processor 650 may be configured to determine the valid force as being lower than the preliminary force.

In yet another example, in order to obtain a desired tooth movement of some of the other teeth 16 in the upper arch form 20, the processor 650 may be configured to determine the valid force as being higher than the preliminary force if the determined induced stress is below the minimum stress threshold for the given other tooth. For example, if the induced stress of the tooth 13 or the tooth 17 is below the minimum stress threshold despite a desired movement of the tooth 13 or the tooth 17, the processor 650 may be configured to increase the preliminary force.

In yet another example, in order to avoid or minimize damage to the tissues of the periodontium 30 of the tooth 15 of the upper arch form 20, the processor 650 may be configured to determine the valid force as being less than the preliminary force if the determined induced stress is above the maximum stress threshold for the tooth 15.

In these examples in which the preliminary force is modulated until a desired outcome is achieved (such as a desirable induced stress level in the tooth 15 or the other teeth 16), the modulated preliminary force is determined to be the valid force.

The processor 650 can then apply the valid force to the start position of the preliminary trajectory segment to obtain the validated end position and hence define the validated trajectory segment.

The processor 650 may be configured to then repeat the above but using the validated end position as the start position of a next preliminary trajectory segment. This can be repeated until all the validated trajectory segments of the trajectory are determined.

In certain embodiments, the processor 650 may be configured to repeat this process based on determined induced stresses associated with another tooth. In certain embodiments, the processor 650 is configured to determine induced stresses associated with all of the upper teeth 16 of the upper arch form 20.

In certain embodiments, if the induced stress associated with the at least other tooth of the upper arch form 20 is determined to be above the minimum stress threshold of that tooth and hence cause that tooth to move, if the movement of that tooth is undesired (according to an input received by the processor 650 for example), the processor 650 may determine that a counter force should be applied to that tooth to prevent or minimize its movement. In this respect, the processor 650 may calculate the counter force that this required to be applied to the other tooth to avoid its movement.

Method

Figure 13:
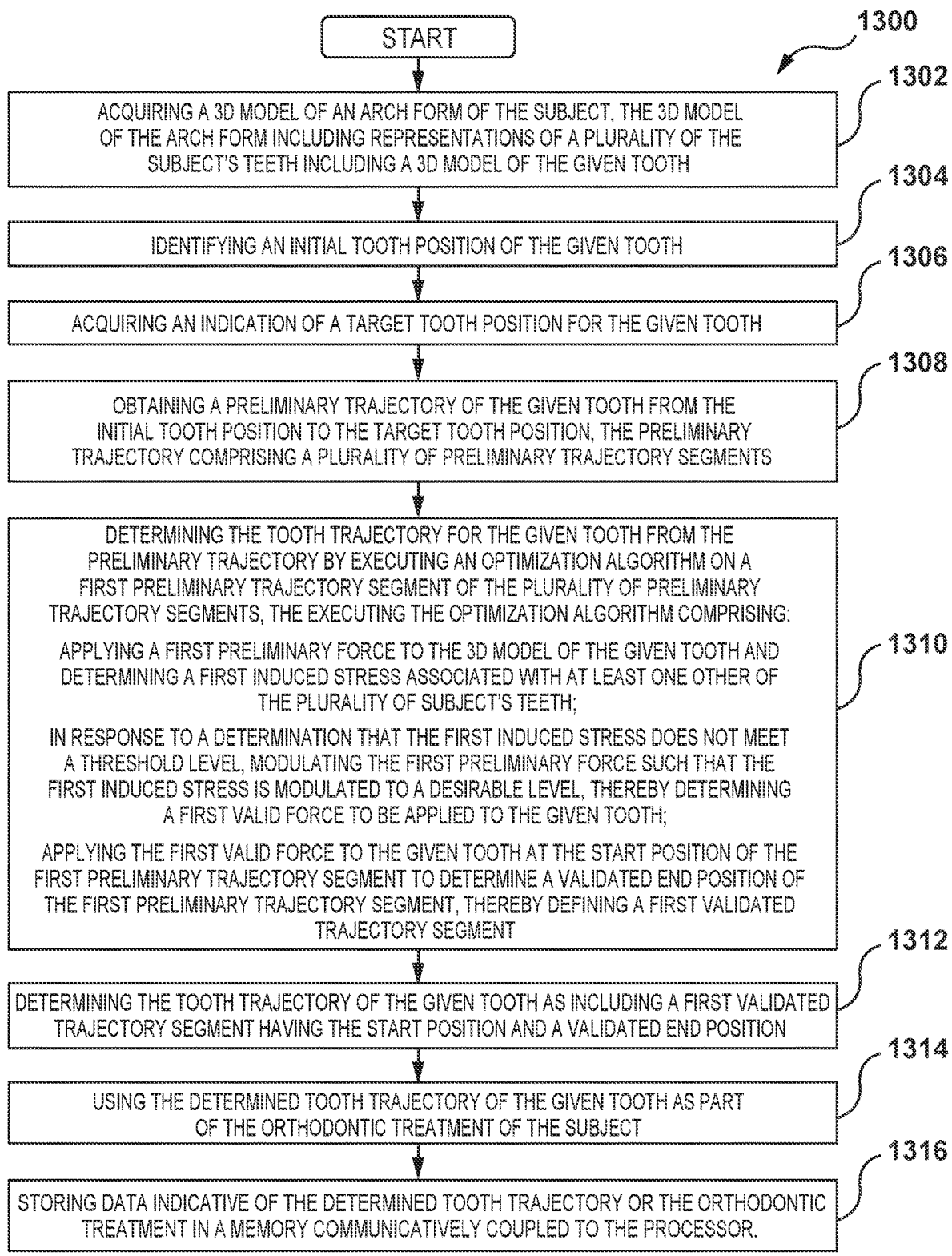
FIG. 13 depicts a flowchart of one aspect of a method for planning the orthodontic treatment based on determining the respective trajectories for the at least some of the subject's teeth of FIG. 1, in accordance with certain embodiments of the present technology.

Given the architecture and the examples provided hereinabove, it is possible to execute a method for determining a tooth trajectory for a given one of patient's teeth (such as the tooth 15 of the upper teeth 16) defining movements thereof during an orthodontic treatment. With reference to FIG. 13, there is depicted a flowchart of one aspect of a method 1300, according to certain non-limiting embodiments of the present technology. The method 1300 can be executed by a processor of a computing environment, such as the processor 650 of the computing environment 640.

Step 1302: Acquiring 3D Digital Model of an Arch Form of the Subject

The method 1300 commences at step 1302 with the processor 650 acquiring a 3D digital model of an arch form of the subject, such as the 3D digital model 700 of the arch form 20. The 3D digital model of the arch form may include representations of a plurality of the subject's teeth including a 3D digital model of a given tooth associated with the subject. For example, in certain non-limiting embodiments of the present technology, using the imaging device 530, the processor 650 may be configured to generate the 3D digital model 700 representative of the upper arch form 20 of the subject, as described above with reference to FIG. 7.

Further, according to some non-limiting embodiments of the present technology, the processor 650 may be configured to generate, based on the 3D digital model 700, respective tooth 3D digital models, for example, of the upper teeth 16—such as the tooth 3D digital model 800 of the tooth 15 (FIG. 8). The processor 650 may be further configured to use the tooth 3D digital model 800 or the 3D digital model 700 for determining a trajectory for the tooth 15 in the course of the orthodontic treatment—such as the second trajectory 1204, as described above with reference to FIG. 12A.

The method 1300 hence advances to step 1304.

Step 1304: Identifying an Initial Position of the Given Tooth

At step 1304, the processor 650 may be configured to identify an initial position of the tooth 15 within the upper arch form 20. In certain embodiments, the processor 650 may use the 3D digital model 700 or the tooth 3D digital model 800. According to certain non-limiting embodiments of the present technology, the processor 650 may be configured to determine 6 DOF of the tooth 3D digital model 800 at the initial moment in time, $<X_2^{init}, t_2^{init}>$, as described above with reference to FIGS. 12A and 12B.

Step 1306: Acquiring an Indication of a Target Position of the Given Tooth

At step 1306, the processor may be configured to acquire a target position of the given tooth, such as from the tooth 3D digital model 800. The target position may be defined as six DOF. For example, the target position for the tooth 15 is indicated as $X_2^{fin}$. According to certain non-limiting embodiments of the present technology, the target position $X_2^{fin}$ may be associated with the aligned position of the tooth 15 within the upper arch form 20.

In some non-limiting embodiments of the present technology, the target position for the tooth 15 may be provided by the clinician. In other non-limiting embodiments of the present technology, the processor 650 may be configured to determine the target position based on averaged data associated with aligned teeth received from a group of subjects.

The method 1300 thus proceeds to step 1308.

Step 1308: Obtaining a Preliminary Trajectory of the Given Tooth from the Initial Tooth Position to the Target Tooth Position, The Preliminary Trajectory Comprising a Plurality of Preliminary Trajectory Segments At step 1308, the processor 650 may be configured to obtain a preliminary trajectory of the tooth 15 from the initial tooth position to the target tooth position. The preliminary trajectory may be the second trajectory 1204 of the tooth 15. The preliminary trajectory may comprise a plurality of preliminary trajectory segments, such as the first trajectory segment TS1, the second trajectory segment TS2 and the third trajectory segment TS3. The preliminary trajectory segments may be determined by the processor 650 in any applicable manner, such as by dividing the trajectory into trajectory segments of equal time, or applying a predetermined time per trajectory segment to the trajectory. The preliminary trajectory segments may also have been determined through a validation process performed by the processor 650, or another processor, such as collision detection.

The method 1300 thus proceeds to step 1310.

Step 1310: Determining the Tooth Trajectory for the Given Tooth from the Preliminary Trajectory by Executing an Optimization Algorithm on a First Preliminary Trajectory Segment of the Plurality of Preliminary Trajectory Segments At step 1310, according to certain non-limiting embodiments of the present technology, the processor 650 may be configured to determine the tooth trajectory for the given tooth from the preliminary trajectory by executing an optimization algorithm on a first preliminary trajectory segment of the plurality of preliminary trajectory segments. For the given tooth 15, the tooth trajectory may be one or more of the validated trajectory segments VTS1, VTS2 and VTS3.

In certain embodiments, the optimization algorithm comprises applying a first preliminary force to the 3D digital model of the given tooth to displace the given tooth from a start position to an end position of the first preliminary trajectory segment within a predetermined time interval. For the given tooth 15, the start position is $X_2^{init}$ and the end position is $t_2^{interm1}$.

Next, the processor 650 may determine a first induced stress associated with at least one other of the plurality of subject's teeth, such as the tooth 13 and the tooth 17. The first induced stress may be determined by the processor 650 according to method described above with reference to "transfer forces".

In response to a determination that the first induced stress does not meet a threshold level, the processor 650 may modulate the first preliminary force such that the first induced stress is modulated to a desirable level, thereby determining a first valid force to be applied to the given tooth. The threshold level may have been determined or obtained by the processor 650 according to methods described above with reference to stress threshold levels and FIGS. 10 and 11.

The processor 650 can then apply the first valid force to the given tooth, such as the tooth 15, at the start position $X_2^{init}$ of the first preliminary trajectory segment, such as TS1, to determine a validated end position, such as $t_2^{Vinterim1}$, of the first preliminary trajectory segment, TS1, thereby defining a first validated trajectory segment, such as VTS1 (FIG. 12B). The processor 650 may thus determine the tooth trajectory of the given tooth as including the first validated trajectory segment having the start position and the validated end position.

The method 1300 thus proceeds to step 1312.

Step 1312: Storing Data Indicative of the Determined Tooth Trajectory or the Orthodontic Treatment in a Memory Communicatively Coupled to the Processor At step 1312, according to certain non-limiting embodiments of the present technology, the processor 650 may be configured to store, for example, in the solid-state drive 660, data indicative of the determined tooth trajectory, such as each one of the plurality of segments associated with the second trajectory 1204 for further planning the orthodontic treatment.

The method thus proceeds to step 1314.

Step 1314: Using the Tooth Trajectory for the Given Tooth for Planning the Orthodontic Treatment of the Subject According to certain non-limiting embodiments of the present technology, the processor 650, may be configured to used the determined tooth trajectory to plan the orthodontic treatment. For example, the tooth trajectory of the other teeth may be determined and the aligner 10 designed and generated for imparting the orthodontic treatment.

According to certain non-limiting embodiments of the present technology, for planning the orthodontic treatment, the processor 650 may be configured to represent the so determine trajectories (such as the first trajectory 1202, the second trajectory 1204, and the third trajectory 1206) in a form of a schedule, such as the planned schedule 1200 depicted in FIG. 12A.

In some non-limiting embodiments of the present technology, each of the predetermined treatment segments may be associated with using a respective configuration of the aligner 10 configured to apply, during a respective one of the plurality of predetermined treatment segments.

Thus, certain embodiments of the method 1300 allow developing more efficient and safer orthodontic treatments. More specifically, applying the method 1300 for planning the orthodontic treatment may allow (1) avoiding application of forces that may cause damage to tissues of periodontium associated with respective ones of the subject's teeth; (2) avoiding application of forces that may cause damage to tissues of periodontium associated with respective other ones of the subject's teeth; while (3) maximizing displacements of each of the respective ones of the subject's teeth, thereby reducing a number of associated aligners to be used in the course of the planned orthodontic treatment.

The method 1300 hence terminates.

Figure 14:
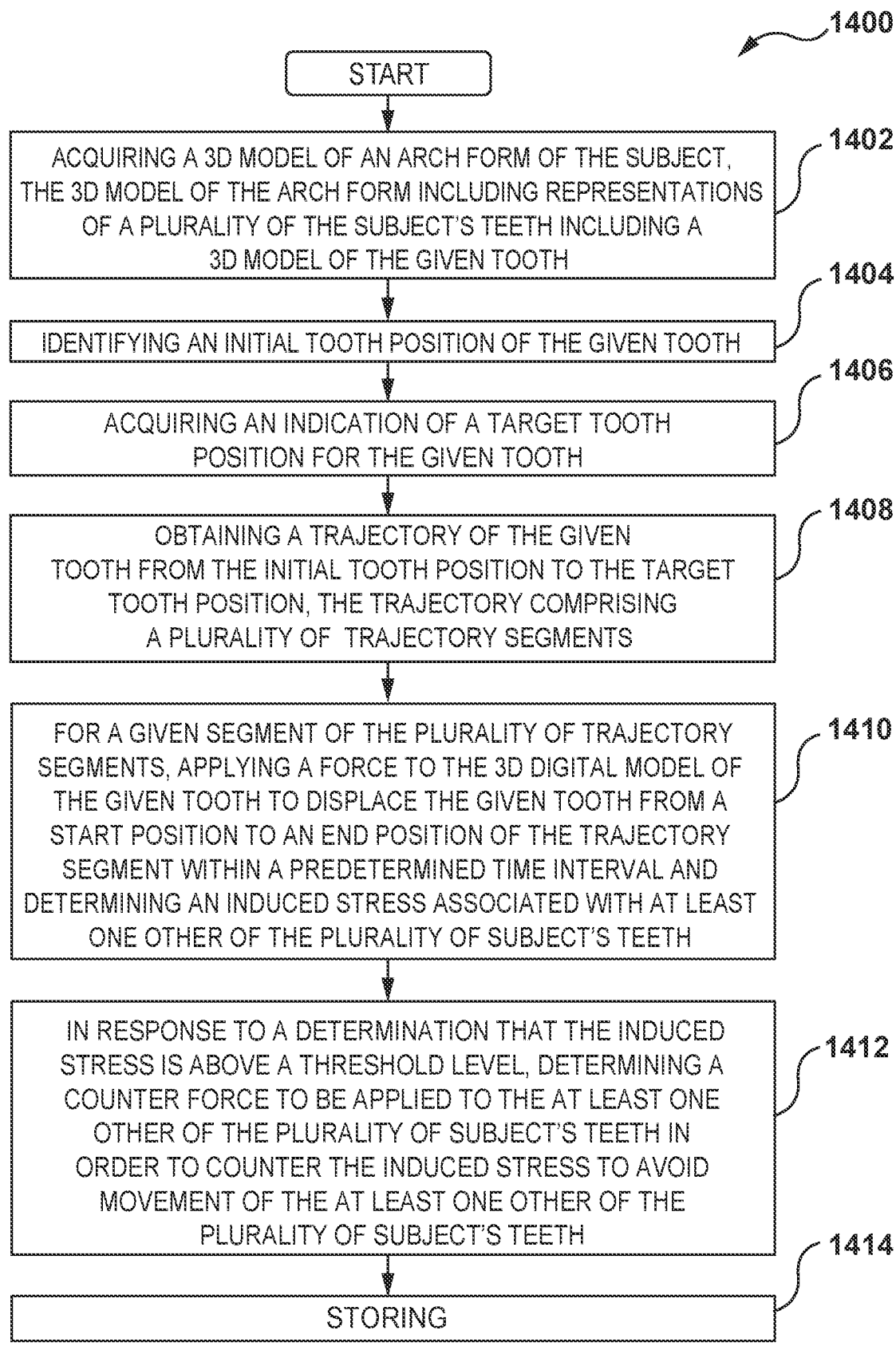
FIG. 14 depicts a flowchart of another aspect of the method for planning the orthodontic treatment based on determining the respective trajectories for the at least some of the subject's teeth of FIG. 1, in accordance with certain embodiments of the present technology.

With reference to FIG. 14, there is depicted a flowchart of another aspect of a method 1400, according to certain non-limiting embodiments of the present technology. The method 1400 can be executed by a processor of a computing environment, such as the processor 650 of the computing environment 640.

Step 1402: Acquiring 3D Digital Model of an Arch Form

The method 1400 commences at step 1402 with the processor 650 acquiring a 3D digital model of an arch form of the subject, the 3D digital model including representations of a plurality of the subject's teeth, such as the upper teeth 16, including for example a 3D digital model of a given tooth. For example, in certain non-limiting embodiments of the present technology, using data from the imaging device 530, the processor 650 may be configured to generate the 3D digital model 700 representative of the upper arch form 20 of the subject, as described above with reference to FIG. 7, and including a representation of the tooth 15.

Further, according to some non-limiting embodiments of the present technology, the processor 650 may be configured to generate, based on the 3D digital model 700, respective tooth 3D digital models, for example, of the upper teeth 16—such as the tooth 3D digital model 800 of the tooth 15 (FIG. 8). The processor 650 may be further configured to use the tooth 3D digital model 800 for determining a trajectory for the tooth 15 in the course of the orthodontic treatment—such as the second trajectory 1204, as described above with reference to FIG. 12A.

The method 1400 hence advances to step 1404.

Step 1404: Identifying an Initial Position of the Given Tooth

At step 1404, the processor 650 may be configured to identify an initial position of the tooth 15 within the upper arch form 20. To that end, according to certain non-limiting embodiments of the present technology, the processor 650 may be configured to determine the initial position based on the 3D digital model 700 or the tooth 3D digital model 800. In certain embodiments, the initial position may be defined as six DOF of the tooth 15 at the initial moment in time, $\langle X_2^{init}, t_2^{init} \rangle$, such as described above with reference to FIGS. 12A and 12B.

The method 1400 thus proceeds to step 1406.

Step 1406: Acquiring an Indication of a Target Position of the Given Tooth

At step 1406, the processor 650 may be configured to acquire a target position of the tooth 15, which may be defined as a six DOF of the tooth in the 3D digital model 700 or the tooth 3D digital model 800 (such as $X_2^{fin}$). According to certain non-limiting embodiments of the present technology, the target position $X_2^{fin}$ may be associated with the aligned position of the tooth 15 within the upper arch form 20.

In some non-limiting embodiments of the present technology, the target position for the tooth 15 may be provided by the clinician. In other non-limiting embodiments of the present technology, the processor 650 may be configured to determine the target position based on averaged data associated with aligned teeth received from a group of subjects.

The method 1400 thus proceeds to step 1408.

Step 1408: Obtaining a Trajectory of the Given Tooth from the Initial Tooth Position to the Target Tooth Position, The Trajectory Comprising a Plurality of Trajectory Segments At step 1408, the processor 650 may be configured to obtain a trajectory of the tooth 15 from the initial tooth position to the target tooth position. The trajectory may be the second trajectory 1204 of the tooth 15. The trajectory may comprise a plurality of trajectory segments, such as the first trajectory segment TS1, the second trajectory segment TS2 and the third trajectory segment TS3. The trajectory segments may be determined by the processor 650 in any applicable manner, such as by dividing the trajectory into trajectory segments of equal time, or applying a predetermined time per trajectory segment to the trajectory. The preliminary trajectory segments may also have been determined through a validation process performed by the processor 650, or another processor, such as collision detection.

The method 1400 thus proceeds to step 1410.

Step 1410: For a Given Segment of the Plurality of Trajectory Segments, Applying a Force to the 3D Digital Model of the Given Tooth to Displace the Given Tooth from a Start Position to an End Position of the Trajectory Segment within a Predetermined Time Interval and Determining an Induced Stress Associated with at Least One Other of the Plurality of Subject's Teeth At step 1410, according to certain non-limiting embodiments of the present technology, the processor 650 may be configured to simulate in the 3D digital model, a force being applied to the given tooth, such as the tooth 15, to move it from a start position to an end position of the trajectory segment. For the given tooth 15, the tooth trajectory segment may be one or more of the validated trajectory segments VTS1, VTS2 and VTS3.

In certain embodiments, the processor 650 may be configured to determine the force to be applied to move the given tooth from the start position to the end position in the tooth trajectory segment. The determination may be based on the movement occurring within a predetermined time interval. For the given tooth 15, the start position may be $X_2^{init}$ and the end position may be $t_2^{interm1}$.

Next, the processor 650 may determine an induced stress associated with at least one other of the plurality of subject's teeth, such as the tooth 13 and/or the tooth 17. The induced stress may be determined by the processor 650 according to method described above with reference to "transfer forces". The processor 650 may be configured to determine the induced stress associated with all the upper teeth 16 as a result of the force 40 applied to the given tooth 15.

The method 1400 thus proceeds to step 1412.

Step 1412: In Response to A Determination that the Induced Stress is Above a Threshold Level, Determining a Counter Force to be Applied to the at Least One Other of the Plurality of Subject's Teeth in Order to Counter the Induced Stress to Avoid Movement of the at Least One Other of the Plurality of Subject's Teeth In response to a determination that the induced stress is above a threshold level, the processor 650 may determine a counter force to be applied to the at least one other of the teeth 16.

The threshold level may be based on an induced movement of the at least one other of the teeth 16 from the induced stress. In some cases, any induced movement of the at least one other of the teeth 16 may not be desirable or wanted, the threshold level being set relatively low. In other cases, some induced movement of the at least one other of the teeth 16 may be tolerated within the planned orthodontic treatment, the threshold level being set relatively higher.

The threshold level may also be based on a potential damage to the PDL of the at least one other of the teeth 16 from the induced stress.

The threshold level may have been determined or obtained by the processor 650 according to methods described above with reference to stress threshold levels and FIGS. 10 and 11.

The processor 650 may be configured to determine the counter force based on a desired outcome related to the at least one other of the teeth 16. For example, the counter force may be determined based on fully countering the induced movement of the at least one other of the teeth 16 from the induced stress. In other examples, the counter force may be determined based on partially countering the induced movement of the at least one other of the teeth 16 from the induced stress. In yet other examples, the counter force may be determined based on directing the induced movement of the at least one other of the teeth 16 from the induced stress, in terms of a direction of movement.

The processor 650 may thus be configured to determine the orthodontic treatment as including the force applied to the given tooth and the counter force applied to the at least one other of the plurality of subject's teeth.

The method thus proceeds to step 1414.

Step 1414: Storing Data Indicative of the Determined Orthodontic Treatment in a Memory Communicatively Coupled to the Processor At step 1414, according to certain non-limiting embodiments of the present technology, the processor 650 may be configured to store, for example, in the solid-state drive 660, data indicative of the determined orthodontic treatment relating to the treatment segment.

According to certain non-limiting embodiments of the present technology, the processor 650, may be configured to use the determined force and the determined counter force to design and manufacture an orthodontic appliance, such as the aligner 10, to apply the determined force and the determined counter force in the treatment segment.

According to certain non-limiting embodiments of the present technology, the processor 650 may be configured to repeat at least some of the abovementioned steps for determining induced stresses for other teeth of the same arch form.

According to certain non-limiting embodiments of the present technology, the processor 650 may be configured to repeat at least some of the abovementioned steps for other treatment segments of the trajectory.

According to certain non-limiting embodiments of the present technology, the processor 650 may be configured to repeat at least some of the abovementioned steps for other trajectories of other teeth of the subject.

The processor 650 may be configured to represent the so determine trajectories (such as the first trajectory 1202, the second trajectory 1204, and the third trajectory 1206) in a form of a schedule, such as the planned schedule 1200 depicted in FIG. 12A.

In some non-limiting embodiments of the present technology, each of the predetermined treatment segments may be associated with using a respective configuration of the aligner 10 configured to apply, during a respective one of the plurality of predetermined treatment segments.

Thus, certain embodiments of the method 1400 allow developing more efficient and safer orthodontic treatments.

More specifically, applying the method 1400 for planning the orthodontic treatment may take into account induced movements of teeth from induced stresses and avoid unwanted movements.

The method 1400 hence terminates.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method for determining an orthodontic treatment for a tooth of a subject, the method being executable by a processor of an electronic device, the method comprising:
   acquiring a 3D digital model of an arch form of the subject, the 3D digital model of the arch form including representations of a plurality of the subject's teeth including:
   a 3D digital model of the given tooth;
   an initial tooth position of the given tooth;
   an indication of a target tooth position for the given tooth; and
   a trajectory of the given tooth defining a path thereof from the initial tooth position to the target tooth position, the trajectory comprising a plurality of trajectory segments,
      a given trajectory segment being associated with a force value of a force to be applied to the given tooth to cause a movement thereof along the given trajectory segment;
   determining whether application of the force to the 3D digital model of the given tooth causes an induced stress associated with at least one other of the plurality of the subject's teeth;
   in response to a determination that the induced stress is outside of a predetermined threshold level, whereby the induced stress causes a movement of the at least one other of the plurality of the subject's teeth, determining a counter force to be applied thereto so as to modulate the movement thereof; and
   storing data indicative of the given trajectory segment including data of the force to be applied to the given tooth and that of the determined counter force to be applied to the at least one other of the plurality of the subject's teeth in a memory communicatively coupled to the processor.

2. The method of claim 1, wherein the predetermined threshold level comprises a minimum stress threshold above which the at least one other of the plurality of the subject's teeth is caused to move.

3. The method of claim 2, wherein the counter force is determined so as to reduce a movement of the at least one other of the plurality of the subject's teeth.

4. The method of claim 2, wherein the counter force is determined so as to direct a movement of the at least one other of the plurality of the subject's teeth.

5. The method of claim 1, further comprising determining the force to be applied to the 3D digital model of the given tooth, the determining comprising:
   obtaining a minimum stress threshold for the given tooth, the minimum stress threshold comprising a minimum amount of stress required to cause the given tooth to move;
   obtaining a maximum stress threshold for the given tooth, the maximum stress threshold comprising a minimum amount of stress which would cause permanent damage to soft tissues around the given tooth; and
   determining the force as that which induces a stress in the given tooth between the minimum stress threshold and the maximum stress threshold.

6. The method of claim 5, further comprising determining one or both of the minimum stress threshold and the maximum stress threshold of the given tooth using a finite element analysis (FEA) method.

7. The method of claim 1, further comprising using the force and the determined counter force for determining the orthodontic treatment for the subject.

8. The method of claim 1, wherein the predetermined threshold level is determined based on a minimum stress threshold of a respective one of the other of the plurality of the subject's teeth, and a maximum stress threshold of the respective one of the other of the plurality of the subject's teeth, the minimum stress threshold comprising a minimum amount of stress required to cause the given respective tooth to move, and the maximum stress threshold comprising a minimum amount of stress which would cause permanent damage to soft tissues around the given respective tooth.

9. The method of claim 8, further comprising determining one or both of the minimum stress threshold and the maximum stress threshold of the given respective tooth using a finite element method on the given respective tooth.

10. The method of claim 1, further comprising displaying, on a display of the electronic device, the determined orthodontic treatment of the trajectory segment.

11. The method of claim 1, further comprising causing a manufacture of an orthodontic aligner according to the determined orthodontic treatment.

12. A system for determining an orthodontic treatment for a tooth of a subject, the system comprising a processor of an electronic device, the processor being configured to execute a method comprising:
   acquiring a 3D digital model of an arch form of the subject, the 3D digital model of the arch form including representations of a plurality of the subject's teeth including:
   a 3D digital model of the given tooth;
   an initial tooth position of the given tooth;
   an indication of a target tooth position for the given tooth; and
   a trajectory of the given tooth defining a path thereof from the initial tooth position to the target tooth position, the trajectory comprising a plurality of trajectory segments,
      a given trajectory segment being associated with a force value of a force to be applied to the given tooth to cause a movement thereof along the given trajectory segment;
   determining whether application of the force to the 3D digital model of the given tooth causes an induced stress associated with at least one other of the plurality of the subject's teeth;
   in response to a determination that the induced stress is outside of a predetermined threshold level, whereby the induced stress causes a movement of the at least one other of the plurality of the subject's teeth, determining a counter force to be applied thereto so as to modulate the movement thereof; and
   storing data indicative of the given trajectory segment including data of the force to be applied to the given tooth and that of the determined counter force to be applied to the at least one other of the plurality of the subject's teeth in a memory communicatively coupled to the processor.

13. A method for determining a tooth trajectory in orthodontic treatment for a tooth of a subject, the method being executable by a processor of an electronic device, the method comprising:

acquiring a 3D digital model of an arch form of the subject, the 3D digital model of the arch form including representations of a plurality of the subject's teeth including:
a 3D digital model of the given tooth;
an initial tooth position of the given tooth;
an indication of a target tooth position for the given tooth; and
a preliminary trajectory of the given tooth from the initial tooth position to the target tooth position, the preliminary trajectory comprising a plurality of preliminary trajectory segments,
the plurality of preliminary trajectory segments having been determined so as to minimize a number of segments required to move the given tooth from the initial tooth position to the target tooth position;

determining the tooth trajectory for the given tooth from the preliminary trajectory by applying thereto an optimization algorithm, such that:
a given validated trajectory segment of the tooth trajectory is associated to a respective valid force to be applied to the given tooth to cause a movement thereof along the given validated trajectory segment, the respective valid force not causing stress to at least one other of the plurality of the subject's teeth greater than a desirable level of stress; using the determined tooth trajectory of the given tooth as part of the orthodontic treatment of the subject; and storing data indicative of the determined tooth trajectory or the orthodontic treatment in a memory communicatively coupled to the processor.

14. The method of claim 13, wherein the desirable level of stress has been determined based on a minimum stress threshold of a respective one of the other of the plurality of the subject's teeth, and a maximum stress threshold of the respective one of the other of the plurality of the subject's teeth, the minimum stress threshold comprising a minimum amount of stress required to cause the given respective tooth to move, and the maximum stress threshold comprising a minimum amount of stress which would cause permanent damage to soft tissues around the given respective tooth.

15. The method of claim 13, wherein applying the optimization algorithm to a respective preliminary trajectory segment of the preliminary trajectory to generate the given validated trajectory segment of the tooth trajectory comprises:

applying a given preliminary force to the 3D digital model of the given tooth to displace the given tooth from a start position to an end position of the respective preliminary trajectory segment within a predetermined time interval;
determining an induced stress associated with at least one other of the plurality of the subject's teeth;
in response to a determination that the induced stress does not meet a threshold level, modulating the given preliminary force such that the induced stress is modulated to the desirable level of stress, thereby determining the respective valid force to be applied to the given tooth; and
applying the respective valid force to the given tooth at the start position of the respective preliminary trajectory segment to determine a validated end position of the respective preliminary trajectory segment, thereby defining the given validated trajectory segment.

16. The method of claim 15, further comprising determining the given preliminary force to be applied to the 3D model of the given tooth, the determining comprising:

obtaining a minimum stress threshold for the given tooth, the minimum stress threshold comprising a minimum amount of stress required to cause the given tooth to move;
obtaining a maximum stress threshold for the given tooth, the maximum stress threshold comprising a minimum amount of stress which would cause permanent damage to soft tissues around the given tooth; and
determining the given preliminary force as being a force which would induce a stress in the given tooth between the minimum stress threshold and the maximum stress threshold.

17. The method of claim 13, further comprising displaying, on a display of the electronic device, the determined orthodontic treatment of the trajectory segment.

* * * * *